United States Patent
Brem et al.

(10) Patent No.: US 11,980,631 B2
(45) Date of Patent: May 14, 2024

(54) β-LACTAMASE INHIBITORS

(71) Applicant: Oxford University Innovation Limited, Oxford (GB)

(72) Inventors: Jürgen Brem, Oxford (GB); Christopher J. Schofield, Oxford (GB); Samuel T. Cahill, Oxford (GB); Karina Calvopina, Oxford (GB); Philip Hinchcliffe, Oxford (GB); Ricky Cain, Oxford (GB); James Spencer, Oxford (GB); Collin W. G. Fishwick, Oxford (GB); Matthew B. Avison, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 16/614,052

(22) PCT Filed: May 18, 2018

(86) PCT No.: PCT/GB2018/051353
§ 371 (c)(1),
(2) Date: Nov. 15, 2019

(87) PCT Pub. No.: WO2018/211289
PCT Pub. Date: Nov. 22, 2018

(65) Prior Publication Data
US 2021/0275552 A1 Sep. 9, 2021

(30) Foreign Application Priority Data
May 18, 2017 (GB) ..................................... 1708002

(51) Int. Cl.
*A61K 31/69* (2006.01)
*A61K 31/407* (2006.01)
(Continued)

(52) U.S. Cl.
CPC ............ *A61K 31/69* (2013.01); *A61K 31/407* (2013.01); *A61K 31/427* (2013.01);
(Continued)

(58) Field of Classification Search
CPC .... A61K 31/69; A61K 31/407; A61K 31/427; A61K 31/431; A61K 31/546; A61P 31/04
See application file for complete search history.

(56) References Cited

U.S. PATENT DOCUMENTS

| | | |
|---|---|---|
| 2015/0361108 A1 | 12/2015 | Burns et al. |
| 2016/0326189 A1 | 11/2016 | Burns et al. |

FOREIGN PATENT DOCUMENTS

| | | | |
|---|---|---|---|
| CN | 105801610 A | 7/2016 | |
| WO | 2016/149393 A1 | 9/2016 | |
| WO | WO-2016149393 A1 * | 9/2016 | ............ A61K 31/69 |

OTHER PUBLICATIONS

Adam, D., The Journal of International Medical Research 2002, vol. 30 (Suppl 1): pp. 10A-19A (Year: 2002).*
(Continued)

*Primary Examiner* — Craig D Ricci
*Assistant Examiner* — Janet L Coppins
(74) *Attorney, Agent, or Firm* — Thomas|Horstemeyer, LLP

(57) ABSTRACT

The present invention relates to the use of certain β-lactamase inhibitors in conjunction with one or more ⊕-lactam antibiotics for the treatment of *Strenotrophomonas maltophilia*, tuberculosis or *Pseudomonas* species infections.

7 Claims, 4 Drawing Sheets

(51) Int. Cl.
  *A61K 31/427* (2006.01)
  *A61K 31/431* (2006.01)
  *A61K 31/546* (2006.01)
  *A61P 31/04* (2006.01)
(52) U.S. Cl.
  CPC .......... *A61K 31/431* (2013.01); *A61K 31/546* (2013.01); *A61P 31/04* (2018.01)

(56) References Cited

OTHER PUBLICATIONS

Anderson, Chemistry & Biology 2003, vol. 10, pp. 787-797. (Year: 2003).*
Thiel, Nature Biotechnology vol. 22 No. 5, 2004, pp. 513-519 (Year: 2004).*
International Search Report and Written Opinion for PT/GB2018/051353 dated Jul. 12, 2018, 7 pages.
Search Report for GB 1708002.9 dated Jan. 31, 2018, 5 pages.
Cahill, et al. "Cyclic Boronates Inhibit All Classes of ß-Lactamases." Antimicrobial Agents and Chemotherapy. Jan. 23, 2017; vol. 61, No. 4, 14 pages.

* cited by examiner

β-LACTAMASE INHIBITORS

CROSS-REFERENCE TO RELATED APPLICATIONS

This application is the National Stage of International Application No. PCT/GB2018/051353, filed May 18, 2018, which claims the priority to GB 1708002.9, filed May 18, 2017, which are entirely incorporated herein by reference.

FIELD OF THE INVENTION

The present invention relates to the use of certain β-lactamase inhibitors in conjunction with one or more β-lactam antibiotics for the treatment of Strenotrophomonas maltophilia, tuberculosis or Pseudomonas species infections.

BACKGROUND OF THE INVENTION

The effective treatment of many fatal bacterial infections is underpinned by the administration of a course of β-lactam antibiotics. However, increasing resistance to β-lactam antibiotics is reducing the effectiveness of β-lactam antibiotics, thereby necessitating the need for improved antibiotic treatments.

β-Lactamases are the most commonly encountered cause of resistance to β-lactam antibiotics, which are the most frequently prescribed class of antibacterial drug world-wide [1-3]. β-lactamases render β-lactams inactive through two steps that involve acylation and de-acylation, which ultimately results in hydrolysis of the β-lactam ring[4, 5]. There are hundreds of β-lactamases known, but they can be grouped based on amino acid sequence into the serine β-lactamase (SBL) Classes A, C and D, and the metallo-β-lactamase (MBL) Classes B1, B2 and B3[6, 7]. Clinically useful β-lactamase inhibitors are being sought, but the varying chemistries and active site architectures of the different classes makes the development of cross-class inhibitors extremely challenging [8-10].

Clavulanic acid is an example of a β-lactam-based inhibitor principally of class A SBLs that has been used clinically for many years. Most commonly it is used in combination with penicillin derivatives, such as amoxycillin and ticarcillin, to enhance their bactericidal effects against some β-lactamase-carrying isolates of species such as E. coli and K. pneumoniae [11-14]. Clavulanate (and the related compounds tazobactam and sulbactam) are in effect irreversible inhibitors whose activity arises from fragmentation of the acyl-enzyme complex formed by reaction with the active-site serine nucleophile, to generate inactivated species [15]. In contrast, avibactam is a non-β-lactam-based β-lactamase inhibitor containing a diazobicyclo heterocyclic core structure which acylates SBLs, at least in some cases reversibly, and has a broader spectrum of activity than clavulanic acid. The potency of avibactam against Class A, C and some Class D SBLs is attributed in part to the stabilization of the carbamoyl complex due to formation of a stable acyl-enzyme complex due to interactions with polar residues present in the active site [16-18]. Avibactam has recently been licenced for clinical use in partnership with the oxy-amino cephalosporin ceftazidime, though the combination is not universally efficacious and has no activity against MBL-producing bacteria [17, 19].

One particular bacterial species that displays widespread resistance to almost all known β-lactams is Stenotrophomonas maltophilia. S. maltophilia is one of the most intrinsically drug resistant bacterial species to be encountered in the clinic. It causes serious infections with high mortality rates in immunocompromised and severely debilitated patients, and is a colonizer of the lungs of 30% of cystic fibrosis patients [23, 24]. While S. maltophilia possesses multiple efflux systems [25-28] that reduce the net rate of entry for many antimicrobials, β-lactam resistance arises primarily from production of two β-lactamases, a subclass B3 MBL "L1", which hydrolyses all β-lactams except for the monobactam, aztreonam, and the class A Extended Spectrum SBL (ESBL) "L2", which hydrolyses all first to third generation cephalosporins, all penicillins and aztreonam [29-31]. The combination of L1 and L2, therefore renders S. maltophilia resistant to all β-lactam antibiotics, although in clinical practice, ceftazidime can be useful because most clinical isolates do not produce enough β-lactamase to cause resistance [32, 33]. However, resistant mutants rapidly emerge through hyper-production of L1 and L2, via single site mutations either in the L1/L2 transcriptional activator, ampR, or in several possible genes whose products influence AmpR [33, 34]. Accordingly, S. maltophilia represents one of the most challenging targets for β-lactam/β-lactamase inhibitor combinations.

There therefore remains a need for new and effective combination therapeutic products that are effective in the treatment of bacterial infections, such as, for example, S. maltophilia bacterial infections.

The treatment of tuberculosis is also a significant challenge [see, for example, Kasik, J. E, Am. Rev. Respir. Dis. 91, 117-119 (1965); Flores, A. R. et al., Microbiology 151, 521-532 (2005); Chambers, H. F. et al., Clin. Infect. Dis. 26, 874-877 (1998); Donald, P. R. Scand. J. Infect. Dis. 33, 466-469 (2001)] along with Pseudomonas infections (which can be common in cystic fibrosis patients), so novel therapies to treat these infections are also required.

The present invention was devised with the foregoing in mind.

SUMMARY OF THE INVENTION

The present invention relates to the use of the particular cyclic boronate β-lactamase inhibitors defined herein for the treatment of Strenotrophomonas maltophilia, tuberculosis or Pseudomonas infections (suitably for the treatment of Strenotrophomonas maltophilia infections).

Thus, in one aspect, the present invention provides a β-lactamase inhibitor of Formula I as defined herein, or a pharmaceutically acceptable salt thereof, for use in combination with a β-lactam antibiotic for the treatment of an infection caused by Strenotrophomonas maltophilia, tuberculosis and/or Pseudomonas species (suitably for the treatment of an infection caused by Strenotrophomonas maltophilia species).

In another aspect, the present invention provides the use of a β-lactamase inhibitor of Formula I, as defined herein, or a pharmaceutically acceptable salt thereof, in the manufacture of a medicament for use in the treatment of Strenotrophomonas maltophilia, tuberculosis and/or Pseudomonas infections in combination with a β-lactam antibiotic (suitably for use in the treatment of Strenotrophomonas maltophilia infection in combination with a β-lactam antibiotic).

In another aspect, the present invention provides a method of treating a Strenotrophomonas maltophilia, tuberculosis and/or Pseudomonas infection, the method comprising administering to a patient in need of such treatment a β-lactamase inhibitor of Formula I as defined herein, or a pharmaceutically acceptable salt thereof, in combination with a β-lactam antibiotic. In an embodiment, present invention provides a method of treating a *Strenotrophomonas maltophilia* infection, the method comprising administering to a patient in need of such treatment a β-lactamase inhibitor of Formula I as defined herein, or a pharmaceutically acceptable salt thereof, in combination with a β-lactam antibiotic.

In yet another aspect, the present invention provides a method of sensitising *Strenotrophomonas maltophilia*, tuberculosis and/or *Pseudomonas* to treatment with a β-lactam antibiotic, the method comprising the administration of a β-lactamase inhibitor of Formula I as defined herein, or a pharmaceutically acceptable salt thereof, in combination with the β-lactam antibiotic. In an embodiment, the present invention provides a method of sensitising *Strenotrophomonas maltophilia* to treatment with a β-lactam antibiotic, the method comprising the administration of a β-lactamase inhibitor of Formula I as defined herein, or a pharmaceutically acceptable salt thereof, in combination with the β-lactam antibiotic.

In yet another aspect, the present invention provides a method of potentiating the effect of a β-lactam antibiotic for the treatment of *Strenotrophomonas maltophilia*, tuberculosis and/or *Pseudomonas* infections, the method comprising the administration of a β-lactamase inhibitor of Formula I as defined herein, or a pharmaceutically acceptable salt thereof, in combination with the β-lactam antibiotic. In an embodiment, the present invention provides a method of potentiating the effect of a β-lactam antibiotic for the treatment of *Strenotrophomonas maltophilia* infections, the method comprising the administration of a β-lactamase inhibitor of Formula I as defined herein, or a pharmaceutically acceptable salt thereof, in combination with the β-lactam antibiotic.

The present invention also provides a combination product comprising a β-lactamase inhibitor of Formula I as defined herein, or a pharmaceutically acceptable salt thereof, and a β-lactam antibiotic. In particular, there is provided a combination product comprising a β-lactamase inhibitor of Formula I as defined herein, or a pharmaceutically acceptable salt thereof, and a β-lactam antibiotic in association with a pharmaceutically acceptable adjuvant, diluent or carrier.

The combination product of the invention is for use in the treatment of *Strenotrophomonas maltophilia*, tuberculosis and/or *Pseudomonas* infections. Suitably, the combination product of the invention is for use in the treatment of *Strenotrophomonas maltophilia* infections.

The combination product of the present invention provides for the administration of a β-lactamase inhibitor of Formula I as defined herein, or a pharmaceutically acceptable salt thereof, and a β-lactam antibiotic. The combination product may be in the form of a combined preparation of the β-lactamase inhibitor and the β-lactam antibiotic. The combination product may also include one or more additional antibiotics or β-lactamase inhibitors. Alternatively, the combination product may comprise a kit of parts comprising separate formulations of the β-lactamase inhibitor and β-lactam antibiotic. The separate formulations of the β-lactamase inhibitor and β-lactam antibiotic may be administered sequentially, separately and/or simultaneously. In one embodiment, the separate formulations of the β-lactamase inhibitor and β-lactam antibiotic of the combination product are administered simultaneously (optionally repeatedly). In another embodiment, the separate formulations of the β-lactamase inhibitor and β-lactam antibiotic of the combination product are administered sequentially (optionally repeatedly). In another embodiment, the separate formulations of the β-lactamase inhibitor and β-lactam antibiotic of the combination product are administered separately (optionally repeatedly). Where the administration of the separate formulations of the β-lactamase inhibitor and β-lactam antibiotic of the combination product is sequential or separate, the delay in administering the second formulation should not be such as to lose the beneficial effect of the combination therapy. Thus, the present invention provides a combination product comprising a β-lactamase inhibitor, or a pharmaceutically-acceptable salt thereof, and a β-lactam antibiotic, or a pharmaceutically-acceptable salt thereof, for use sequentially, separately and/or simultaneously in the treatment of *Strenotrophomonas maltophilia*, tuberculosis and/or *Pseudomonas* infections (suitably in the treatment of *Strenotrophomonas maltophilia* infections).

In another aspect, the present invention relates to a pharmaceutical composition suitable for use in the treatment of a *Strenotrophomonas maltophilia*, tuberculosis and/or *Pseudomonas* infection which comprises a combination therapeutic product, as defined herein, in association with a pharmaceutically-acceptable excipient or carrier. In an embodiment, present invention relates to a pharmaceutical composition suitable for use in the treatment of a *Strenotrophomonas maltophilia* infection which comprises a combination therapeutic product, as defined herein, in association with a pharmaceutically-acceptable excipient or carrier.

In another aspect, there is provided a combination product which comprises a kit of parts comprising the following components:
   a β-lactamase inhibitor, or a pharmaceutically-acceptable salt thereof, in association with a pharmaceutically acceptable adjuvant, diluent or carrier; and
   a β-lactam antibiotic, or a pharmaceutically-acceptable salt thereof, in association with a pharmaceutically acceptable adjuvant, diluent or carrier,
   wherein the components are provided in a form which is suitable for sequential, separate and/or simultaneous administration.

The kit of parts is for the treatment of *Strenotrophomonas maltophilia*, tuberculosis and/or *Pseudomonas* infections (suitably for the treatment of *Strenotrophomonas maltophilia*, infections).

In one embodiment the kit of parts comprises:
   a first container comprising a β-lactamase inhibitor, or a pharmaceutically-acceptable salt thereof, in association with a pharmaceutically acceptable adjuvant, diluent or carrier;
   a second container comprising a β-lactam antibiotic, or a pharmaceutically-acceptable salt thereof, in association with a pharmaceutically acceptable adjuvant, diluent or carrier; and
   a container means for containing said first and second containers.

In one embodiment, the kit of parts further comprises instructions on how to administer the components sequentially, separately and/or simultaneously. In one embodiment, the kit of parts further comprises instructions indicating that the combination product can be used in the treatment of *Strenotrophomonas maltophilia*, tuberculosis and/or *Pseudomonas* infections.

Features, including optional, suitable, and preferred features in relation to one aspect of the invention may also be features, including optional, suitable and preferred features in relation to any other aspect of the invention.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C) alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

An "alkylene" group is an alkyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene (—$CH_2$—), ethylene (—$CH_2CH_2$—), propylene (—$CH_2CH_2CH_2$—), 2-methylpropylene (—$CH_2CH(CH_3)CH_2$—), pentylene (—$CH_2CH_2CH_2CH_2CH_2$—), and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicyclo[2.2.1]heptyl.

"(3-8C)cycloalkyl-(1-2C)alkylene" means a (3-8C)cycloalkyl group covalently attached to a (1-2C)alkylene group, both of which are defined herein.

The term "halo" or "halogeno" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or SO2 groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example Advanced Organic Chemistry, by Jerry March, 4$^{th}$ Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

By "spiro bi-cyclic ring systems" we mean that the two ring systems share one common spiro carbon atom, i.e. the heterocyclic ring is linked to a further carbocyclic or heterocyclic ring through a single common spiro carbon atom. Examples of spiro ring systems include 6-azaspiro[3.4]octane, 2-oxa-6-azaspiro[3.4]octane, 2-azaspiro[3.3]heptanes, 2-oxa azaspiro[3.3]heptanes, 7-oxa-2-azaspiro[3.5]nonane, 6-oxa-2-azaspiro[3.4]octane, 2-oxa azaspiro[3.5]nonane and 2-oxa-6-azaspiro[3.5]nonane.

"Heterocyclyl(1-2C)alkyl" means a heterocyclyl group covalently attached to a (1-2C) alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1 H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1, 3-dihydro-2-benzothienyl, 4,5,6,7-tetrahydrobenzofuranyl, indolinyl, 1,2,3,4-tetrahydro-1,8-naphthyridinyl, 1 ,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from: a benzene ring fused to a 5- or 6-membered ring containing 1, 2 or 3 ring heteroatoms; a pyridine ring fused to a 5- or 6-membered ring containing 1, 2 or 3 ring heteroatoms; a pyrimidine ring fused to a 5- or 6-membered ring containing 1 or 2 ring heteroatoms; a pyrrole ring fused to a 5- or 6-membered ring containing 1, 2 or 3 ring heteroatoms; a pyrazole ring fused to a 5- or 6-membered ring containing 1 or 2 ring heteroatoms; a pyrazine ring fused to a 5- or 6-membered ring containing 1 or 2 ring heteroatoms; an imidazole ring fused to a 5- or 6-membered ring containing 1 or 2 ring heteroatoms; an oxazole ring fused to a 5- or 6-membered ring containing 1 or 2 ring heteroatoms; an isoxazole ring fused to a 5- or 6-membered ring containing 1 or 2 ring heteroatoms; a thiazole ring fused to a 5- or 6-membered ring containing 1 or 2 ring heteroatoms; an isothiazole ring fused to a 5- or 6-membered ring containing 1 or 2 ring heteroatoms; a thiophene ring fused to a 5- or 6-membered ring containing 1, 2 or 3 ring heteroatoms; a furan ring fused to a 5- or 6-membered ring containing 1, 2 or 3 ring heteroatoms; a cyclohexyl ring fused to a 5- or 6-membered heteroaromatic ring containing 1, 2 or 3 ring heteroatoms; and a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(1-2C)alkyl" means a heteroaryl group covalently attached to a (1-2C)alkylene group, both of which are defined herein. Examples of heteroaralkyl groups include pyridin-3-ylmethyl, 3-(benzofuran-2-yl)ethyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(1-2C)alkyl" means an aryl group covalently attached to a (1-2C)alkylene group, both of which are defined herein. Examples of aryl-(1-2C)alkyl groups include benzyl, phenylethyl, and the like.

This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

The term "optionally substituted" refers to either groups, structures, or molecules that are substituted and those that are not substituted. The term "wherein a/any CH, $CH_2$, $CH_3$ group or heteroatom (i.e. NH) within a $R^1$ group is optionally substituted" suitably means that (any) one of the hydrogen radicals of the $R^1$ group is substituted by a relevant stipulated group.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Combination Therapeutic Products of the Present Invention

It will be appreciated by a person skilled in the art that the term "combination therapeutic product" used herein, or references to the use of β-lactamase inhibitors of Formula I, as defined herein, being used "in combination" with a β-lactam antibiotic, refers to the net combined product resulting from the administration one or more the recited components either simultaneously, sequentially or separately, in order to induce a therapeutic effect.

Furthermore, it will be appreciated that in administering the one or more recited components either simultaneously, sequentially or separately, the therapeutic product affords a beneficial therapeutic effect to that achieved upon administration of one of the components of the combination therapeutic product alone, and at its conventional dose. The beneficial therapeutic effect may be measured by, for example, the extent of the response, the response rate, the time to disease progression or the survival period, to that achievable on dosing one of the components of the combination therapeutic product alone, and at its conventional dose.

For example, the effect of the combination therapeutic product is beneficial if the effect is therapeutically improved compared to the effect achievable with the β-lactam antibiotic or β-lactamase inhibitor alone. Further, the effect of the combination therapeutic product is defined as affording a beneficial effect if one of the components is dosed at its conventional dose (or lower) and the other component is dosed at a reduced dose and the therapeutic effect, as measured by, for example, the extent of the response, the response rate, the time to disease progression or the survival period, is equivalent (or higher) to that achievable on dosing conventional amounts of the components of the combination therapeutic product alone.

According to one aspect of the present invention, there is provided a combination therapeutic product comprising one or more β-lactam antibiotics and a compound of Formula I for use simultaneously, sequentially or separately in the treatment of a *Strenotrophomonas maltophilia*, tuberculosis and/or *Pseudomonas* infection, wherein the compound of Formula I has the structural formula given below:

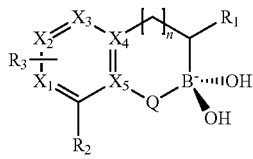
(I)

wherein:
Q is absent or selected from O, CH$_2$, NH or S;
ring atoms X$_1$, X$_2$, X$_3$, X$_4$ and X$_5$ are either all carbon atoms or one or two of X$_1$, X$_2$, X$_3$, X$_4$ and X$_5$ are nitrogen atoms;
n is 0 or 1;
R$_1$ is a substituent group selected from hydrogen, halo, cyano, nitro, hydroxy or a group of the formula:

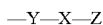

wherein
Y is absent or a linker group of the formula —[CR$^{A1}$R$^{A2}$]$_m$- in which m is an integer selected from 1 or 2, and R$^{A1}$ and R$^{A2}$ are each independently selected from hydrogen or (1-2C)alkyl;
X is absent or —O—, —C(O)—, —C(O)O—, —OC(O)—, —CH(OR$^{A3}$)—, —N(R$^{A3}$)—, —N(R$^{A3}$)—C(O)—, —N(R$^{A3}$)—C(O)O—, —C(O)—N(R$^{A3}$)—, —N(R$^{A3}$)C(O)N(R$^{A3}$)—, —S—, —SO—, —SO$_2$—, —S(O)$_2$N(R$^{A3}$)—, or —N(R$^{A3}$)SO$_2$— wherein R$^{A3}$ is selected from hydrogen or (1-2C)alkyl; and Z is hydrogen, (1-6C)alkyl, (2-6C)alkenyl, (2-6C)alkynyl, aryl, (3-6C)cycloalkyl, (3-6C) cycloalkenyl, heteroaryl or heterocyclyl;

and wherein Z is optionally further substituted by one or more substituent groups independently selected from oxo, halo, cyano, nitro, hydroxy, carboxy, NR$^{A6}$R$^{A7}$, —(CR$^{A4}$R$^{A5}$)$_p$-NR$^{A6}$R$^{A7}$ (wherein p is selected from 1, 2 or 3), (1-4C)alkoxy, (1-4C) alkyl, (3-8C)cycloalkyl, (3-8C)cycloalkyl-(1-3C)alkyl, (1-4C)alkanoyl, (1-4C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, C(O)NR$^{A6}$R$^{A7}$, NR$^{A4}$C(O)R$^{A5}$, NR$^{A4}$S(O)$_2$R$^{A5}$ and S(O)$_2$NR$^{A4}$R$^{A5}$; wherein R$^{A4}$ and R$^{A5}$ are each independently selected from hydrogen or (1-4C)alkyl; R$^{A6}$ and R$^{A7}$ are each independently selected from hydrogen, (1-4C)alkyl, (1-4C)alkylamino, (3-6C)cycloalkyl or (3-6C)cycloalkyl(1-2C) alkyl; or R$^{A6}$ and R$^{A7}$ can be linked such that, together with the nitrogen atom to which they are attached, they form a 4-6 membered heterocyclic ring;

and wherein any alkyl, aryl, heterocyclyl or heteroaryl group present in a substituent group on Z is optionally further substituted by halo, cyano, nitro, hydroxy, caboxy, amino, (1-2C)alkoxy, or (1-2C) alkyl;

R$_2$ is a substituent group selected from hydrogen, halo, cyano, nitro, hydroxy or R$_2$ is selected from:
(i) —C(0)OR$_{2A}$, wherein R$_{2A}$ is selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups selected from oxo, halo, cyano, nitro, hydroxy, carboxy, amino, (1-4C)alkoxy, (1-4C) alkyl, or (1-4C)alkanoyl;
(ii) —C(O)NR$_{2B}$R$_{2C}$; wherein R$_{2B}$ and R$_{2C}$ are each independently selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent selected from oxo, halo, cyano, nitro, hydroxy, carboxy, amino, (1-4C)alkoxy, (1-4C)alkyl, or (1-4C) alkanoyl;
(iii) —C(O)NR$_{2D}$NR$_{2B}$R$_{2C}$; wherein R$_{2D}$ is selected from hydrogen or (1-6C)alkyl and R$_{2B}$ and R$_{2C}$ are as defined above;
(iv) tetrazolyl;
(v) triazolyl;
(vi) —B(OR$_{2F}$)(OR$_{2G}$), wherein R$_{2F}$ and R$_{2G}$ are each independently selected from hydrogen, (1-6C)alkyl or R$_{2F}$ and R$_{2G}$ are linked such that, together with the B and O atoms, they form a 5 or 6-membered heterocyclic ring, which is optionally substituted by (1-2C)alkyl; or
(vii) trifluoromethylketone;

R$_3$ is absent or a substituent group selected from halo, cyano, nitro, hydroxy or a group of the formula:

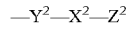

wherein
Y$^2$ is absent or a linker group of the formula —[CR$^{C1}$R$^{C2}$]$_n$- in which n is an integer selected from 1 or 2, and R$^{C1}$ and R$^{C2}$ are each independently selected from hydrogen or (1-2C)alkyl;
X$^2$ is absent or —O—, —C(O)—, —C(O)O—, —OC(O)—, OCH(OR$^{C3}$)—, —N(R$^{C3}$)—, —N(R$^{C3}$)—C(O)—, —N(R$^{C3}$)—C(O)O, —C(O)—N(R$^{C3}$)—, —N(R$^{C3}$)C(O)N(R$^{C3}$)—, —S—, —SO—, —$SO_2$—, —, $S(—)_2N(R^{C3})$—, or —$N(R^{C3})SO_2$—
wherein $R^{C3}$ is selected from hydrogen or (1-2C) alkyl; and $Z^2$ is hydrogen, (1-6C)alkyl, (2-6C)alkenyl, (2-6C) alkynyl, aryl, (3-6C)cycloalkyl, (3-6C)cycloalkenyl, heteroaryl or heterocyclyl;

and wherein $Z^2$ is optionally further substituted by one or more substituent groups independently selected from oxo, halo, cyano, nitro, hydroxy, carboxy, $NR^{C4}R^{C5}$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, $C(O)NR^{C4}R^{C5}$, $NR^{C4}C(O)R^{C5}$, $NR^{C4}S(O)_2R^{C5}$ and $S(O)_2NR^{C4}R^{C5}$; wherein $R^{C4}$ and $R^{C5}$ are each independently selected from hydrogen, (1-4C)alkyl or (3-6C)cycloalkyl or (3-6C)cycloalkyl(1-2C)alkyl; or $R^{C4}$ and $R^{C5}$ can be linked such that, together with the nitrogen atom to which they are attached, they form a 4-6 membered heterocyclic ring;

and wherein any alkyl, aryl, heterocyclyl or heteroaryl group present in a substituent group on $Z^2$ is optionally further substituted by halo, cyano, nitro, hydroxy, caboxy, $NR^{C6}R^{C7}$, (1-2C)alkoxy, or (1-2C) alkyl; wherein $R^{C6}$ and $R^{X7}$ are selected from hydrogen or (1-2C)alkyl;

with the proviso that when n is 0, Q is not absent.
or a pharmaceutically acceptable salt thereof.

According to another aspect of the present invention, there is provided a compound of Formula I for use in the treatment of a *Strenotrophomonas maltophilia*, tuberculosis or *Pseudomonus* infection, wherein the compound is administered in combination with one or more β-lactam antibiotics, and wherein the compound of Formula I is as defined herein.

β-Lactamase Inhibitors

In an embodiment, the compound of Formula I is a β-lactamase inhibitor. That is the compound of Formula I is capable of displaying inhibitory activity towards one or more serine β-lactamases (SBL) and/or metallo-β-lactamases (MBL).

Particular β-lactamase inhibitors of the present invention include, for example, compounds of the Formula I defined above, or pharmaceutically acceptable salts and/or solvates thereof, wherein, unless otherwise stated, each of Q, n, $X_1$, $X_2$, $X_3$, $X_4$, $X_5$, $R_1$, $R_2$, $R_3$, and any associated substituent groups has any of the meanings defined hereinbefore or in any of paragraphs (1) to (32) hereinafter:

(1) Q is absent or selected from O, NH or S;
(2) Q is absent or selected from O or NH;
(3) Q is absent or O;
(4) Q is O;
(5) n is 0;
(6) n is 1;
(7) $X_1$, $X_2$, $X_3$, $X_4$ and $X_5$ are either all carbon atoms or one of $X_1$, $X_2$, $X_3$, $X_4$ and $X_5$ are nitrogen atoms;
(8) $X_1$, $X_2$, $X_3$, $X_4$ and $X_5$ are either all carbon atoms or one or two of $X_1$, $X_2$ are $X_3$ are nitrogen atoms and $X_4$ and $X_5$ are carbon atoms;
(9) $X_1$, $X_2$, $X_3$, $X_4$ and $X_5$ are all carbon atoms;
(10) $R_1$ is a substituent group selected from hydrogen, halo, cyano, nitro, hydroxy or a group of the formula:

—Y—X—Z wherein
Y is absent or a linker group of the formula —$[CR^{A1}R^{A2}]_m$- in which m is an integer selected from 1 or 2, and $R^{A1}$ and $R^{A2}$ are each independently selected from hydrogen or (1-2C)alkyl;

X is absent or —O—, —C(O)—, —C(O)O—, —OC(O)—, —$CH(OR^{A3})$—, —$N(R^{A3})$—, —$N(R^{A3})$—C(O)—, —$N(R^{A3})$—C(O)O—, —C(O)—$N(R^{A3})$—, —$N(R^{A3})C(O)N(R^{A3})$—, —S—, —SO—, —$SO_2$—, —$S(O)_2N(R^{A3})$—, or —$N(R^{A3})SO_2$- wherein $R^{A3}$ is selected from hydrogen or (1-2C)alkyl; and Z is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;

and wherein Z is optionally further substituted by one or more substituent groups independently selected from oxo, halo, cyano, nitro, hydroxy, carboxy, $NR^{46}R^{47}$, —$(CR^{44}R^{45})_p$-$NR^{46}R^{47}$ (wherein p is selected from 1, 2 or 3), (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, heterocyclyl, heterocyclyloxy, heterocyclyl-(1-2C) alkyl, heteroaryl, heteroaryloxy, heteroaryl-(1-2C) alkyl, $C(O)NR^{46}R^{47}$, $NR^{44}C(O)R^{45}$, $NR^{44}S(O)_2R^{45}$ and $S(O)_2NR^{44}R^{45}$; wherein $R^{44}$ and $R^{45}$ are each independently selected from hydrogen or (1-4C)alkyl; $R^{46}$ and $R^{47}$ are each independently selected from hydrogen, (1-4C)alkyl, (1-4C)alkylamino, (3-6C)cycloalkyl or (3-6C)cycloalkyl(1-2C) alkyl; or $R^{46}$ and $R^{47}$ can be linked such that, together with the nitrogen atom to which they are attached, they form a 4-6 membered heterocyclic ring;

(11) $R_1$ is a substituent group selected from hydrogen, halo, cyano, nitro, hydroxy or a group of the formula:

—Y—X—Z wherein
Y is absent or a (1-2C)alkylene;
X is absent or —O—, —C(O)—, —C(O)O—, —OC(O)—, —$N(R^{43})$—, —$N(R^{43})$—C(O)—, —$N(R^{43})$—C(O)O—, —C(O)—$N(R^{43})$—, —$N(R^{43})C(O)N(R^{43})$—, —$S(O)_2N(R^{43})$—, or —$N(R^{43})SO_2$—wherein $R^{43}$ is selected from hydrogen or (1-2C)alkyl; and Z is hydrogen, (1-6C)alkyl, (2-6C)alkenyl, (2-6C)alkynyl, aryl, (3-6C)cycloalkyl, (3-6C) cycloalkenyl, heteroaryl or heterocyclyl;

and wherein Z is optionally further substituted by one or more substituent groups independently selected from oxo, halo, cyano, nitro, hydroxy, carboxy, $NR^{46}R^{47}$, —$(CR^{44}R^{45})_p$—$NR^{46}R^{47}$ (wherein p is selected from 1, 2 or 3), (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, heterocyclyl, heterocyclyloxy, heterocyclyl-(1-2C) alkyl, heteroaryl, heteroaryloxy, heteroaryl-(1-2C) alkyl, $C(O)NR^{46}R^{47}$, $NR^{44}C(O)R^{45}$, $NR^{44}S(O)_2R^{45}$ and $S(O)_2NR^{44}R^{45}$; wherein $R^{44}$ and $R^{45}$ are each independently selected from hydrogen or (1-4C)alkyl; $R^{46}$ and $R^{47}$ are each independently selected from hydrogen, (1-4C)alkyl, (1-4C)alkylamino, (3-6C)cycloalkyl or (3-6C)cycloalkyl(1-2C) alkyl; or $R^{46}$ and $R^{47}$ can be linked such that, together with the nitrogen atom to which they are attached, they form a 4-6 membered heterocyclic ring;

(12) $R_1$ is a substituent group selected from hydrogen, halo, cyano, nitro, hydroxy or a group of the formula:

—Y—X—Z wherein —
Y is absent or a (1-2C)alkylene;
X is absent or —O—, —C(O)—, —C(O)O—, —OC(O)—, —N($R^{43}$)—, —N($R^{43}$)—C(O)—, —N($R^{43}$)—C(O)O—, —C(O)—N($R^{43}$)—, —N($R^{43}$)C(O)N($R^{43}$)—, —SO$_2$—, —S(O)$_2$N($R^{43}$)—, or —N($R^{43}$)SO$_2$—wherein $R^{43}$ is selected from hydrogen or (1-2C)alkyl; and
Z is hydrogen, (1-6C)alkyl, (2-6C)alkenyl, (2-6C)alkynyl, aryl, (3-6C)cycloalkyl, (3-6C) cycloalkenyl, heteroaryl or heterocyclyl;
and wherein Z is optionally further substituted by one or more substituent groups independently selected from oxo, halo, cyano, nitro, hydroxy, carboxy, $NR^{46}R^{47}$, —$(CR^{44}R^{45})_p$—$NR^{46}R^{47}$ (wherein p is selected from 1, 2 or 3), (1-4C)alkoxy, (1-4C)alkyl, (3-8C)cycloalkyl, (3-8C)cycloalkyl-(1-3C)alkyl, (1-4C)alkanoyl, aryl, aryloxy, heterocyclyl, heterocyclyl-(1-2C)alkyl, heteroaryl or heteroaryl-(1-2C)alkyl; wherein $R^{44}$ and $R^{45}$ are each independently selected from hydrogen or (1-4C)alkyl; $R^{46}$ and $R^{47}$ are each independently selected from hydrogen, (1-4C)alkyl, (1-4C)alkylamino, (3-6C)cycloalkyl or (3-6C)cycloalkyl(1-2C)alkyl; or $R^{46}$ and $R^{47}$ can be linked such that, together with the nitrogen atom to which they are attached, they form a 4-6 membered heterocyclic ring;

(13) $R_1$ is a substituent group selected from hydrogen, halo, cyano, nitro, hydroxy or a group of the formula:

—Y—X—Z wherein
Y is absent or a (1-2C)alkylene;
X is absent or —o—, —C(O)—, —C(O)O—, —OC(O)—, —N($R^{43}$)—, —N($R^{43}$)—C(O)—, —N($R^{43}$)—C(O)O—, —C(O)—N($R^{43}$)—, —N($R^{43}$)C(O)N($R^{43}$)—, —SO$_2$—, -S(O)$_2$N($R^{43}$)—, or —N($R^{43}$)SO$_2$—wherein $R^{43}$ is selected from hydrogen or (1-2C)alkyl; and
Z is hydrogen, (1-6C)alkyl, (2-6C)alkenyl, (2-6C)alkynyl, aryl, (3-6C)cycloalkyl, (3-6C) cycloalkenyl or heterocyclyl;
and wherein Z is optionally further substituted by one or more substituent groups independently selected from oxo, halo, cyano, nitro, hydroxy, carboxy, $NR^{46}R^{47}$, —$(CR^{44}R^{45})_p$—$NR^{46}R^{47}$ (wherein p is selected from 1, 2 or 3), (1-4C)alkoxy, (1-4C)alkyl, (3-8C)cycloalkyl, (3-8C)cycloalkyl-(1-3C)alkyl, (1-4C)alkanoyl, aryl, aryloxy, heterocyclyl, heterocyclyl-(1-2C)alkyl, heteroaryl or heteroaryl-(1-2C)alkyl; wherein $R^{44}$ and $R^{45}$ are each independently selected from hydrogen or (1-4C)alkyl; $R^{46}$ and $R^{47}$ are each independently selected from hydrogen, (1-4C)alkyl, (1-4C)alkylamino, (3-6C)cycloalkyl or (3-6C)cycloalkyl(1-2C)alkyl; or $R^{46}$ and $R^{47}$ can be linked such that, together with the nitrogen atom to which they are attached, they form a 4-6 membered heterocyclic ring;

(14) $R_1$ is a substituent group selected from hydrogen, halo, cyano, nitro, hydroxy or a group of the formula:

—Y—X—Z wherein
Y is absent or a (1-2C)alkylene;
X is absent or —O—, —C(O)—, —C(O)O—, —OC(O)—, —N($R^{43}$)—, —N($R^{43}$)—C(O)—, —N($R^{43}$)—C(O)O—, —C(O)—N($R^{43}$)—, —N($R^{43}$)C(O)N($R^{43}$)—, —S(O)$_2$N($R^{43}$)—, or —N($R^{43}$)SO$_2$—wherein $R^{43}$ is selected from hydrogen or (1-2C)alkyl; and
Z is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein Z is optionally further substituted by one or more substituent groups independently selected from oxo, halo, cyano, nitro, hydroxy, carboxy, $NR^{46}R^{47}$, —$(CR^{44}R^{45})_p$—$NR^{46}R^{47}$ (wherein p is selected from 1, 2 or 3), (1-4C)alkoxy, (1-4C)alkyl, (3-8C)cycloalkyl, (3-8C)cycloalkyl-(1-3C)alkyl, (1-4C)alkanoyl, aryl, aryloxy, heterocyclyl, heterocyclyl-(1-2C)alkyl, heteroaryl or heteroaryl-(1-2C)alkyl; wherein $R^{44}$ and $R^{45}$ are each independently selected from hydrogen or (1-4C)alkyl; $R^{46}$ and $R^{47}$ are each independently selected from hydrogen, (1-4C)alkyl, (1-4C)alkylamino, (3-6C)cycloalkyl or (3-6C)cycloalkyl(1-2C)alkyl; or $R^{46}$ and $R^{47}$ can be linked such that, together with the nitrogen atom to which they are attached, they form a 4-6 membered heterocyclic ring;

(15) $R_1$ is a substituent group selected from hydrogen, halo, cyano, nitro, hydroxy or a group of the formula:

—Y—X—Z wherein
Y is absent or a (1-2C)alkylene;
X is absent or —O—, —C(O)—, —C(O)O—, —OC(O)—, —N($R^{43}$)—, —N($R^{43}$)—C(O)—, —N($R^{43}$)—C(O)O—, —C(O)—N($R^{43}$)—, —N($R^{43}$)C(O)N($R^{43}$)—, —S(O)$_2$—, —S(O)$_2$N($R^{43}$)—, or —N($R^{43}$)SO$_2$—wherein $R^{43}$ is selected from hydrogen or (1-2C)alkyl; and
Z is hydrogen, (1-6C)alkyl, (2-6C)alkenyl, (2-6C)alkynyl, aryl, (3-6C)cycloalkyl or (3-6C)cycloalkenyl;
and wherein Z is optionally further substituted by one or more substituent groups independently selected from oxo, halo, cyano, nitro, hydroxy, carboxy, $NR^{46}R^{47}$, —$(CR^{44}R^{45})_p$—$NR^{46}R^{47}$ (wherein p is selected from 1, 2 or 3), (1-4C)alkoxy, (1-4C)alkyl, (3-8C)cycloalkyl, (3-8C)cycloalkyl-(1-3C)alkyl, (1-4C)alkanoyl, aryl, aryloxy, heterocyclyl, heterocyclyl-(1-2C)alkyl, heteroaryl or heteroaryl-(1-2C)alkyl; wherein $R^{44}$ and $R^{45}$ are each independently selected from hydrogen or (1-4C)alkyl; $R^{46}$ and $R^{47}$ are each independently selected from hydrogen, (1-4C)alkyl, (1-4C)alkylamino, (3-6C)cycloalkyl or (3-6C)cycloalkyl(1-2C)alkyl; or $R^{46}$ and $R^{47}$ can be linked such that, together with the nitrogen atom to which they are attached, they form a 4-6 membered heterocyclic ring;

(16) $R_1$ is a substituent group selected from hydrogen, halo, cyano, nitro, hydroxy or a group of the formula:

—Y—X—Z wherein
Y is absent or a (1-2C)alkylene;
X is —C(O)—, —C(O)O—, —OC(O)—, —N($R^{43}$)—, —N($R^{43}$)—C(O)—or —C(O)—N($R^{43}$)—, wherein $R^{43}$ is selected from hydrogen or (1-2C)alkyl; and
Z is hydrogen, (1-6C)alkyl, aryl, (3-6C)cycloalkyl, (3-6C)cycloalkenyl, heteroaryl or heterocyclyl;

and wherein Z is optionally further substituted by one or more substituent groups independently selected from oxo, halo, cyano, nitro, hydroxy, carboxy, $NR^{46}R^{47}$, $—(CR^{44}R^{45})_p—NR^{46}R^{47}$ (wherein p is selected from 1, 2 or 3), (1-4C)alkoxy, (1-4C)alkyl, (3-8C)cycloalkyl, (3-8C)cycloalkyl-(1-3C)alkyl, (1-4C)alkanoyl, aryl, aryloxy, heterocyclyl, heterocyclyl-(1-2C)alkyl, heteroaryl or heteroaryl-(1-2C)alkyl; wherein $R^{44}$ and $R^{45}$ are each independently selected from hydrogen or (1-4C)alkyl; $R^{46}$ and $R^{47}$ are each independently selected from hydrogen, (1-4C)alkyl, (1-4C)alkylamino, (3-6C)cycloalkyl or (3-6C)cycloalkyl(1-2C)alkyl; or $R^{46}$ and $R^{47}$ can be linked such that, together with the nitrogen atom to which they are attached, they form a 4-6 membered heterocyclic ring;

(17) $R_1$ is a substituent group selected from hydrogen, halo, cyano, nitro, hydroxy or a group of the formula:

—X—Z wherein

X is —OC(O)—, —N($R^{43}$)—C(O)— or —C(O)—N($R^{43}$)—, wherein $R^{43}$ is selected from hydrogen or (1-2C)alkyl; and Z is hydrogen, (1-6C)alkyl, aryl, (3-6C)cycloalkyl, (3-6C)cycloalkenyl, heteroaryl or heterocyclyl;

and wherein Z is optionally further substituted by one or more substituent groups independently selected from oxo, halo, cyano, nitro, hydroxy, carboxy, $NR^{46}R^{47}$, $—(CR^{44}R^{45})_p—NR^{46}R^{47}$ (wherein p is selected from 1, 2 or 3), (1-4C)alkoxy, (1-4C)alkyl or (1-4C)alkanoyl; wherein $R^{44}$ and $R^{45}$ are each independently selected from hydrogen or (1-4C)alkyl; $R^{46}$ and $R^{47}$ are each independently selected from hydrogen, (1-4C)alkyl, (1-4C)alkylamino, (3-6C)cycloalkyl or (3-6C)cycloalkyl(1-2C)alkyl; or $R^{46}$ and $R^{47}$ can be linked such that, together with the nitrogen atom to which they are attached, they form a 4-6 membered heterocyclic ring;

(18) $R_1$ is a substituent group selected from hydrogen, halo, cyano, nitro, hydroxy or a group of the formula:

—X—Z wherein

X is —OC(O)—, —N($R^{43}$)—C(O)— or —C(O)—N($R^{43}$)-, wherein $R^{43}$ is selected from hydrogen or (1-2C)alkyl; and Z is hydrogen, (1-6C)alkyl, aryl, (3-6C)cycloalkyl or (3-6C)cycloalkenyl;

and wherein Z is optionally further substituted by one or more substituent groups independently selected from oxo, halo, cyano, nitro, hydroxy, carboxy, $NR^{46}R^{47}$, $—(CR^{44}R^{45})_p—NR^{46}R^{47}$ (wherein p is selected from 1, 2 or 3), (1-4C)alkoxy, (1-4C)alkyl or (1-4C)alkanoyl; wherein $R^{44}$ and $R^{45}$ are each independently selected from hydrogen or (1-4C)alkyl; $R^{46}$ and $R^{47}$ are each independently selected from hydrogen, (1-4C)alkyl, (1-4C)alkylamino, (3-6C)cycloalkyl or (3-6C)cycloalkyl(1-2C)alkyl; or $R^{46}$ and $R^{47}$ can be linked such that, together with the nitrogen atom to which they are attached, they form a 4-6 membered heterocyclic ring;

(19) $R_1$ is a substituent group of the formula:

—X—Z wherein

X is —OC(O)—, —N($R^{43}$)—C(O)— or —C(O)—N($R^{43}$)—, wherein $R^{43}$ is selected from hydrogen or (1-2C)alkyl; and Z is (1-6C)alkyl, aryl, (3-6C)cycloalkyl, (3-6C)cycloalkenyl, heteroaryl or heterocyclyl;

and wherein Z is optionally further substituted by one or more substituent groups independently selected from oxo, halo, cyano, nitro, hydroxy, carboxy, $NR^{46}R^{47}$, $—(CR^{44}R^{45})_p—NR^{46}R^{47}$ (wherein p is selected from 1, 2 or 3), (1-4C)alkoxy, (1-4C)alkyl or (1-4C)alkanoyl; wherein $R^{44}$ and $R^{45}$ are each independently selected from hydrogen or (1-4C)alkyl; $R^{46}$ and $R^{47}$ are each independently selected from hydrogen, (1-4C)alkyl, (1-4C)alkylamino or (3-6C)cycloalkyl;

(20) $R_1$ is a substituent group of the formula:

—X—Z wherein

X is —N($R^{43}$)—C(O)—, wherein $R^{43}$ is selected from hydrogen or (1-2C)alkyl; and Z is (1-6C)alkyl, aryl, (3-6C)cycloalkyl, heteroaryl or heterocyclyl;

and wherein Z is optionally further substituted by one or more substituent groups independently selected from oxo, halo, cyano, nitro, hydroxy, carboxy, $NR^{46}R^{47}$, $—(CH_2)_p—NR^{46}R^{47}$ (wherein p is selected from 1 or 2), (1-4C)alkoxy, (1-4C)alkyl or (1-4C)alkanoyl; wherein $R^{46}$ and $R^{47}$ are each independently selected from hydrogen, (1-4C)alkyl or (1-4C)alkylamino;

(21) $R_1$ is a substituent group of the formula:

—X—Z wherein

X is —N($R^{43}$)—C(O)—, wherein $R^{43}$ is selected from hydrogen or (1-2C)alkyl; and Z is (1-6C)alkyl, aryl, (3-6C)cycloalkyl or heterocyclyl;

and wherein Z is optionally further substituted by one or more substituent groups independently selected from oxo, halo, cyano, nitro, hydroxy, carboxy, $NR^{46}R^{47}$, $—(CH_2)_p—NR^{46}R^{47}$ (wherein p is selected from 1 or 2), (1-4C)alkoxy, (1-4C)alkyl or (1-4C)alkanoyl; wherein $R^{46}$ and $R^{47}$ are each independently selected from hydrogen, (1-4C)alkyl or (1-4C)alkylamino;

(22) $R_1$ is a substituent group of the formula:

—X—Z wherein

X is —N($R^{43}$)—C(O)—, wherein $R^{43}$ is selected from hydrogen or (1-2C)alkyl; and Z is (1-6C)alkyl, aryl or (3-6C)cycloalkyl;

and wherein Z is optionally further substituted by one or more substituent groups independently selected from oxo, halo, cyano, nitro, hydroxy, carboxy, $NR^{46}R^{47}$, $—(CH_2)_p—NR^{46}R^{47}$ (wherein p is selected from 1 or 2), (1-4C)alkoxy, (1-4C)alkyl or (1-4C)alkanoyl; wherein $R^{46}$ and $R^{47}$ are each independently selected from hydrogen, (1-4C)alkyl or (1-4C)alkylamino;

(23) $R_2$ is a substituent group selected from hydrogen, halo, cyano, nitro, hydroxy or $R_2$ is selected from:

(i) —C(O)O$R_{2A}$, wherein $R_{2A}$ is selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups selected from oxo, halo, cyano, nitro, hydroxy, carboxy, amino, (1-4C)alkoxy, (1-4C)alkyl, or (1-4C)alkanoyl;
(ii) —C(O)NR$_{2B}$R$_{2C}$; wherein R$_{2B}$ and R$_{2C}$ are each independently selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent selected from oxo, halo, cyano, nitro, hydroxy, carboxy, amino, (1-4C)alkoxy, (1-4C)alkyl, or (1-4C)alkanoyl;
(iii) —C(O)NR$_{2D}$NR$_{2B}$R$_{2C}$; wherein R$_{2D}$ is selected from hydrogen or (1-6C)alkyl and R$_{2B}$ and R$_{2C}$ are as defined above;
(iv) tetrazolyl;
(v) triazolyl;
(vi) trifluoromethylketone;
(24) R$_2$ is a substituent group selected from hydrogen, halo, cyano, nitro, hydroxy or R$_2$ is selected from:
(i) —C(O)OR$_{2A}$, wherein R$_{2A}$ is selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups selected from oxo, halo, cyano, nitro, hydroxy, carboxy, amino, (1-4C)alkoxy, (1-4C)alkyl, or (1-4C)alkanoyl;
(ii) —C(O)NR$_{2B}$R$_2$; wherein R$_{2B}$ and R$_{2C}$ are each independently selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent selected from oxo, halo, cyano, nitro, hydroxy, carboxy, amino, (1-4C)alkoxy, (1-4C)alkyl, or (1-4C)alkanoyl;
(iii) tetrazolyl; or
(iv) triazolyl;
(25) R$_2$ is a substituent group selected from hydrogen, halo, cyano, nitro, hydroxy or R2 is selected from:
(i) —C(O)OR$_{2A}$, wherein R$_{2A}$ is selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups selected from oxo, halo, cyano, nitro, hydroxy, carboxy, amino, (1-4C)alkoxy, (1-4C)alkyl, or (1-4C)alkanoyl; or
(ii) —C(O)NR$_{2B}$R$_{2C}$; wherein R$_{2B}$ and R$_{2C}$ are each independently selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent selected from oxo, halo, cyano, nitro, hydroxy, carboxy, amino, (1-4C)alkoxy, (1-4C)alkyl, or (1-4C)alkanoyl;
(26) R$_2$ is a substituent group selected from:
(i) —C(O)OR$_{2A}$, wherein R$_{2A}$ is selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups selected from oxo, halo, cyano, nitro, hydroxy, carboxy, amino, (1-4C)alkoxy, (1-4C)alkyl or (1-4C)alkanoyl;
(27) R$_2$ is selected from:
(i) —C(O)OR$_{2A}$, wherein R$_{2A}$ is selected from hydrogen, (1-6C)alkyl or (3-8C)cycloalky;
(28) R$_2$ is COOH, triazolyl or tetrazolyl;
(29) R$_3$ is absent or a substituent group selected from halo, cyano, nitro, hydroxy or a group of the formula:

—Y$^2$—X$^2$—Z$^2$ wherein
Y$^2$ is absent or a linker group of the formula —[CR$^{C1}$R$^{Cr}$]$_n$— in which n is an integer selected from 1 or 2, and R$^{C1}$ and R$^{C2}$ are each independently selected from hydrogen or (1-2C)alkyl;
X$^2$ is absent or —O—, —C(O)—, —C(O)O—, —OC(O)—, —CH(OR$^{C3}$)—, —N(R$^{C3}$)—, —N(R$^{C3}$)—C(O)—, —N(R$^{C3}$)—C(O)O, —C(O)-N(R$^{C3}$)—, —N(R$^{C3}$)C(O)N(R$^{C3}$)—, —S—, —SO—, —SO$_2$—, —S(O)$_2$N(R$^{C3}$)—, or —N(R$^{C3}$)SO$_2$— wherein R$^{C3}$ is selected from hydrogen or (1-2C)alkyl; and
Z$^2$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein Z$^2$ is optionally further substituted by one or more substituent groups independently selected from oxo, halo, cyano, nitro, hydroxy, carboxy, NR$^{C4}$R$^{C5}$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, C(O)NR$^{C4}$R$^{C5}$, NR$^{C4}$C(O)R$^{C5}$, NR$^{C4}$S(O)$_2$R$^{C5}$ and S(O)$_2$NR$^{C4}$R$^{C5}$; wherein R$^{C4}$ and R$^{C5}$ are each independently selected from hydrogen, (1-4C)alkyl or (3-6C)cycloalkyl or (3-6C)cycloalkyl(1-2C)alkyl; or R$^{C4}$ and R$^{C5}$ can be linked such that, together with the nitrogen atom to which they are attached, they form a 4-6 membered heterocyclic ring;
(30) R$_3$ is absent or a substituent group selected from halo, cyano, nitro, hydroxy or a group of the formula:

—Y$^2$—X$^2$—Z$^2$ wherein
Y$^2$ is absent;
X$^2$ is absent or —O—, —C(O)—, —C(O)O—, —OC(O)—, —N(R$^{C3}$)—, —N(R$^{C3}$)—C(O)—or C(O)—N(R$^{C3}$)—, wherein R$^{C3}$ is selected from hydrogen or (1-2C)alkyl; and
Z$^2$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein Z$^2$ is optionally further substituted by one or more substituent groups independently selected from oxo, halo, cyano, nitro, hydroxy, carboxy, amino, (1-4C)alkoxy, (1-4C)alkyl, (3-8C)cycloalkyl or (1-4C)alkanoyl;
(31) R$_3$ is absent or a substituent group selected from halo, cyano, nitro, hydroxy, carboxy, amino, (1-4C)alkoxy, (1-4C)alkyl, (3-8C)cycloalkyl or (1-4C)alkanoyl;
(32) R$_3$ is absent.
In particular embodiments of the compounds of the Formula I, one or more of the following provisos may apply:
i) when R$_1$ is a group of the following formula:

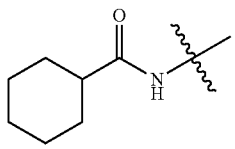 [SMILES: *NC(=O)C1CCCCC1]

$R_2$ is not $COOCH_3$; and/or ii) when $R^2$ is COOH, $X^1$-$X^5$ are carbon atoms, $R^3$ is absent and n is 1, $R^1$ is not an aminomethyl substituted pyridinyl.

Suitably, a heteroaryl or heterocyclyl group as defined herein is a monocyclic heteroaryl or heterocyclyl group comprising one, two or three heteroatoms selected from N, O or S.

Suitably, a heteroaryl is a 5- or 6-membered heteroaryl ring comprising one, two or three heteroatoms selected from N, O or S.

Suitably, a heterocyclyl group is a 4-, 5-, 6- or 7-membered heterocyclyl ring comprising one, two or three heteroatoms selected from N, O or S. Most suitably, a heterocyclyl group is a 5-, 6- or 7-membered ring comprising one, two or three heteroatoms selected from N, O or S [e.g. morpholinyl (e.g. 4-morpholinyl), pyridinyl, piperazinyl, homopiperazinyl or pyrrolidinonyl].

Suitably an aryl group is phenyl.

Suitably, Q is as defined in any one of paragraphs (1) to (4) above. Most suitably, Q is as defined in paragraph (4) above.

Suitably, n is as defined in any one of paragraphs (5) to (6) above.

Suitably, X, $X_2$, $X_3$, $X_4$ and $X_5$ are as defined in any one of paragraphs (7) to (9) above. Most suitably, $X_1$, $X_2$, $X_3$, $X_4$ and $X_5$ is as defined in paragraph (9) above.

Suitably, $R_1$ is as defined in any one of paragraphs (10) to (22) above. Most suitably, $R_1$ is as defined in paragraph (22) above.

Suitably, $R_2$ is as defined in any one of paragraphs (23) to (28) above. Most suitably, $R_2$ is as defined in paragraph (28) above.

Suitably, $R_3$ is as defined in any one of paragraphs (29) to (32) above. Most suitably, $R_3$ is as defined in paragraph (32) above.

In a particular group of compounds of Formula (I), $X_4$ and $X_5$ are carbon, i.e. the compounds have the structural formula Ia (a sub-definition of Formula I) shown below:

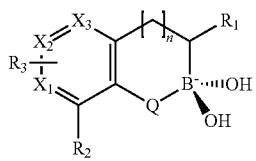

Formula Ia wherein Q, n, $X_1$, $X_2$, $X_3$, $R_1$, $R_2$ and $R_3$ are as defined hereinabove.

In an embodiment of the compounds of Formula Ia:
Q is as defined in any one of paragraphs (1) to (4) above;
n is as defined in any one of paragraphs (5) to (6) above;
$X_1$, $X_2$ and $X_3$ are as defined in any one of paragraphs (7) to (9) above;
$R_1$ is as defined in any one of paragraphs (10) to (22) above;
$R_2$ is as defined in any one of paragraphs (23) to (28) above; and
$R_3$ is as defined in any one of paragraphs (29) to (32) above.

In another embodiment of the compounds of Formula Ia:
Q is as defined in paragraph (4) above;
n is as defined in paragraph (6) above;
$X_1$, $X_2$ and $X_3$ are as defined in paragraph (9) above;
$R_1$ is as defined in paragraph (22) above;
$R_2$ is as defined in paragraph (28) above; and
$R_3$ is as defined in paragraph (32) above.

In a particular group of compounds of Formula (I), Q is O and $X_4$ and $X_5$ are carbon, i.e. the compounds have the structural formula Ib (a sub-definition of Formula I) shown below:

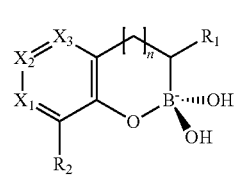

Formula Ib wherein n, $X_1$, $X_2$, $X_3$, $R_1$, $R_2$ and $R_3$ are as defined hereinabove.

In an embodiment of the compounds of Formula Ib:
n is as defined in any one of paragraphs (5) to (6) above;
$X_2$ and $X_3$ are as defined in any one of paragraphs (7) to (9) above;
$R_1$ is as defined in any one of paragraphs (10) to (22) above;
$R_2$ is as defined in any one of paragraphs (23) to (28) above; and
$R_3$ is as defined in any one of paragraphs (29) to (32) above.

In another embodiment of the compounds of Formula Ib:
n is as defined in paragraph (6) above;
$X_1$, $X_2$ and $X_3$ are as defined in paragraph (9) above;
$R_1$ is as defined in paragraph (22) above;
$R_2$ is as defined in paragraph (28) above; and
$R_3$ is as defined in paragraph (32) above.

In a particular group of compounds of Formula (I), Q is O, $R_3$ is absent, and $X_1$, $X_2$, $X_3$, $X_4$ and $X_5$ are carbon, i.e. the compounds have the structural formula Ic (a sub-definition of Formula I) shown below:

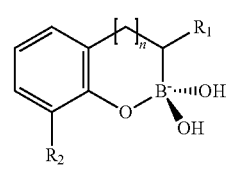

Formula Ic wherein n, $R_1$ and $R_2$ are as defined hereinabove.

In an embodiment of the compounds of Formula Ic:
n is as defined in any one of paragraphs (5) to (6) above;
$R_1$ is as defined in any one of paragraphs (10) to (122) above; and
$R_2$ is as defined in any one of paragraphs (23) to (28) above.

In another embodiment of the compounds of Formula Ic:
n is as defined in paragraph (6) above;

R₁ is as defined in paragraph (12) above; and
R₂ is as defined in paragraph (28) above.

In a particular group of compounds of Formula (I), Q is O, R₃ is absent, X₁, X₂, X₃, X₄ and X₅ are carbon and R₁ and R₂ are of the formula shown below, i.e. the compounds have the structural formula Id (a sub-definition of Formula I) shown below:

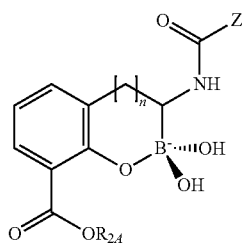

Formula Id wherein n, R₂ₐ, and Z are as defined hereinabove.

In an embodiment of the compounds of Formula Id:
n is as defined in any one of paragraphs (5) to (6) above;
Z is as defined in any one of paragraphs (10) to (22) above and
R₂ₐ is as defined in any one of paragraphs (23) to (27) above.

In another embodiment of the compounds of Formula Id:
n is as defined in paragraph (6) above;
Z is as defined in paragraph (22) above and
R₂ₐ is as defined in paragraph (27) above.

In a particular group of compounds of Formula (I), the compounds are enantioenriched, Q is O, R₃ is absent, X₁, X₂, X₃, X₄ and X₅ are carbon and R₁ and R₂ are of the formula shown below, i.e. the compounds have the structural formula Ie (a sub-definition of Formula I) shown below:

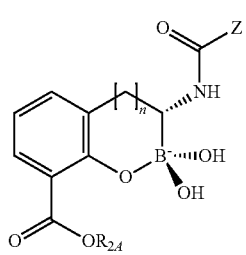

Formula Ie wherein n, R₂ₐ, and Z are as defined hereinabove.

In an embodiment of the compounds of Formula Ie:
n is as defined in any one of paragraphs (5) to (6) above;
Z is as defined in any one of paragraphs (10) to (22) above and
R₂ₐ is as defined in any one of paragraphs (23) to (27) above.

In another embodiment of the compounds of Formula Ie:
n is as defined in paragraph (6) above;
Z is as defined in paragraph (22) above and
R₂ₐ is as defined in paragraph (27) above.

Particular compounds of Formula (I) include any of the compounds exemplified in the present application, or a pharmaceutically acceptable salt or solvate thereof, and, in particular, any of the following:

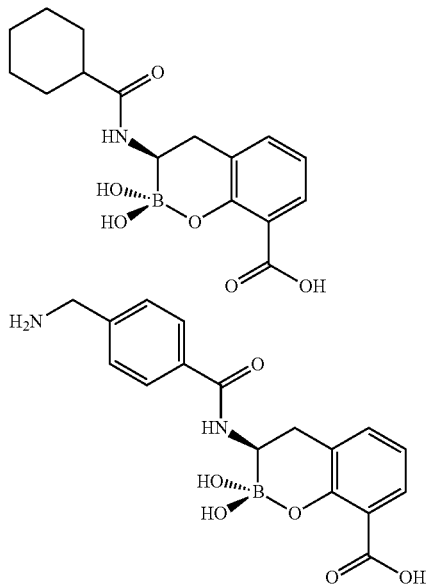

It shall be appreciated that although the compounds of Formula I (or sub-formulae Ia to Ie) depicted hereinabove are shown to comprise a sp₃ hybridised boron atom, it is recognised that this form may be in equilibrium with the sp² hybridised boron form, or in equilibrium with other, including acyclic, forms. For example, it will be appreciated that acyclic tautomers, such as those illustrated below, are also anticipated by the genus of compounds defined by Formula I (and/or sub-formulae Ia to Ie) herein:

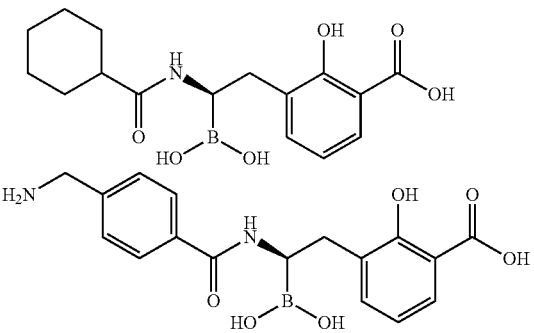

The various functional groups and substituents making up the compounds of Formula I (or sub-formulae Ia to Ie) are typically chosen such that the molecular weight of the compound of Formula I (or sub-formulae Ia to Ie) does not exceed 1000. More usually, the molecular weight of the compound will be less than 900, for example less than 800, or less than 700, or less than 650, or less than 600. More preferably, the molecular weight is less than 550 and, for example, is 500 or less.

A suitable pharmaceutically acceptable salt of a compound of Formula I (or sub-formulae Ia to Ie) is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a cytochrome be inhibitor of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn-lngold-Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of Formula I (or sub-formulae la to le) of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess β-lactamase inhibitory activity.

The present invention also encompasses compounds of Formula I (or sub-formulae la to le) which comprise one or more isotopic substitutions. For example, H may be in any isotopic form, including $^1H$, $^2H(D)$, and $^3H$ (T); C may be in any isotopic form, including $^{12}C$, $^{13}C$, and $^{14}C$; and O may be in any isotopic form, including $^{16}O$ and $^{18}O$; and the like.

It is also to be understood that certain compounds of Formula I (or sub-formulae la to le) may exist in solvated as well as unsolvated forms such as, for example, hydrated forms. It is to be understood that the invention encompasses all such solvated forms that possess β-lactamase inhibitory activity.

Compounds of Formula I (or sub-formulae la to le) may also exist in a number of different tautomeric forms and references to compounds of Formula I (or sub-formulae la to le) include all such forms. For the avoidance of doubt, where a compound can exist in one of several tautomeric forms, and only one is specifically described or shown, all others are nevertheless embraced the structural formula of Formula I (or sub-formulae la to le). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

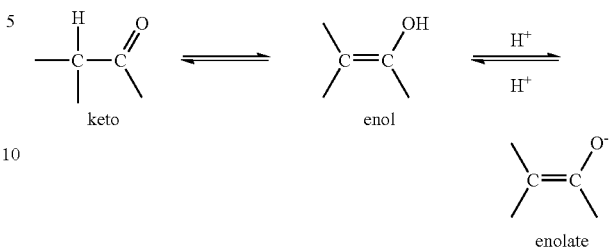

Compounds of Formula I (or sub-formulae la to le) containing an amine function may also form N-oxides. A reference herein to a compounds of Formula I (or sub-formulae la to le) that contains an amine function also includes the N-oxide. Where a compounds of Formula I (or sub-formulae la to le) contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (mCPBA), for example, in an inert solvent such as dichloromethane.

The compounds of Formula I (or sub-formulae la to le) may be administered in the form of a pro-drug which is broken down in the human or animal body to release a compound of Formula I (or sub-formulae la to le) of the invention. A pro-drug may be used to alter the physical properties and/or the pharmacokinetic properties of a compounds of Formula I (or sub-formulae la to le) of the invention. A pro-drug can be formed when the compound of Formula I (or sub-formulae la to le) of the invention contains a suitable group or substituent to which a property-modifying group can be attached. Examples of pro-drugs include in vivo cleavable ester derivatives that may be formed at a carboxy group or a hydroxy group in a compound of the Formula I and in vivo cleavable amide derivatives that may be formed at a carboxy group or an amino group in a β-lactamase inhibitor of Formula I (or sub-formulae la to le).

Accordingly, the present invention includes those compounds of Formula I (or sub-formulae la to le) as defined hereinbefore when made available by organic synthesis and when made available within the human or animal body by way of cleavage of a pro-drug thereof. Accordingly, the present invention includes those compounds of Formula I (or sub-formulae la to le) that are produced by organic synthetic means and also such compounds of Formula I (or sub-formulae la to le) that are produced in the human or animal body by way of metabolism of a precursor compound, that is a compound of Formula I (or sub-formulae la to le) may be a synthetically-produced compound or a metabolically-produced compound.

A suitable pharmaceutically acceptable pro-drug of a compound of Formula I (or sub-formulae la to le) is one that is based on reasonable medical judgement as being suitable for administration to the human or animal body without undesirable pharmacological activities and without undue toxicity.

Various forms of pro-drug have been described, for example in the following documents:
a) Methods in Enzymology, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, Advanced Drug Delivery Reviews, 8, 1-38 (1992);
e) H. Bundgaard, et al., Journal of Pharmaceutical Sciences, 77, 285 (1988);
f) N. Kakeya, et al., Chem. Pharm. Bull., 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of Formula I (or sub-formulae Ia to Ie) that possesses a carboxy group is, for example, an in vivo cleavable ester thereof. An in vivo cleavable ester of a compound of Formula I (or sub-formulae Ia to Ie) containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tent-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of Formula I (or sub-formulae Ia to Ie) that possesses a hydroxy group is, for example, an in vivo cleavable ester or ether thereof. An in vivo cleavable ester or ether of a compound of Formula I (or sub-formulae Ia to Ie) containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of Formula I (or sub-formulae Ia to Ie) that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of Formula I (or sub-formulae Ia to Ie) that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

It shall also be appreciated that the compounds of Formula I (or sub-formulae Ia to Ie) depicted above may also be in one or more prodrug forms which may use to optimise delivery or formulation. For example, the compounds may be synthesised as boronate esters in which the two OH groups attached to the boron are instead OR' groups, wherein each R' is independently a non-hydrogen substituent, e.g. an alkyl group or aryl group, or each R' substituent is linked such that, together with the boron atom to which they are attached, they form a ring (e.g. 5, 6 or 7 membered ring). Examples of suitable R' groups include (1-6C)alkyl groups and examples of groups where each R' substituent is linked include —$CH_2$—or —$CH_2$—$CH_2$—.

The in vivo effects of a compound of Formula I (or sub-formulae Ia to Ie) may be exerted in part by one or more metabolites that are formed within the human or animal body after administration of a compound of Formula I (or sub-formulae Ia to Ie). As stated hereinbefore, the in vivo effects of a compound of Formula I (or sub-formulae Ia to Ie) may also be exerted by way of metabolism of a precursor compound (a pro-drug).

Compounds of Formula I (or sub-formulae Ia to Ie) may be prepared by techniques known in the art.

β-Lactam Antibiotics

It will understood by the person skilled in the art that any suitable β-lactam antibiotic or analogue thereof may be used in the present invention. Non limiting examples of suitable β-lactam antibiotics include carbapenems (e.g. meropenem, faropenem, imipenem, ertapenem, doripenem, panipenem/betamipron and biapenem as well as razupenem, tebipenem, lenapenem and tomopenem), ureidopenicillins (e.g. piperacillin), carbacephems (e.g. loracarbef) and cephalosporins (e.g. cefpodoxime, ceftazidime, cefotaxime, ceftriaxone, ceftobiprole, and ceftaroline). Specific examples of suitable β-lactam antibacterial agents include, for example, aztreonam, temocillin, piperacillin, cefpodoxime, ceftazidime, cefotaxime, ceftriaxone, meropenem, faropenem, imipenem, loracarbef, ceftobiprole and ceftaroline.

In an embodiment, the β-lactam antibiotic is selected from azetreonam, ceftazidime, meropenem, ertrapenem or faropenem.

Pharmaceutical Compositions

References herein to pharmaceutical compositions refer to compositions comprising a therapeutic agent as defined herein, or a pharmaceutically acceptable salt or solvate thereof, in association with a pharmaceutically acceptable diluent or carrier. For example, solid oral forms may contain, together with the active compound, diluents, such as, for example, lactose, dextrose, saccharose, cellulose, corn starch or potato starch; lubricants, such as, for example, silica, talc, stearic acid, magnesium or calcium stearate, and/or polyethylene glycols; binding agents; such as, for example, starches, arabic gums, gelatin, methylcellulose, carboxymethylcellulose or polyvinyl pyrrolidone; disaggregating agents, such as, for example, starch, alginic acid, alginates or sodium starch glycolate; effervescing mixtures; dyestuffs; sweeteners; wetting agents, such as, for example, lecithin, polysorbates, laurylsulphates; and, in general, non-toxic and pharmacologically inactive substances used in pharmaceutical formulations. Such pharmaceutical compositions may be manufactured in by conventional methods known in the art, such as, for example, by mixing, granulating, tableting, sugar coating, or film coating processes.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing). Suitably, oral or parenteral administration is preferred. Most suitably, oral administration is preferred.

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat a condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the condition, the age and sex of the animal or patient and the route of administration, according to well-known principles of medicine.

In using a compound of the Formula I as defined herein for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention relates to the discovery that the compounds of Formula I defined herein are particularly useful agents for potentiating the effects of β-lactam antibiotics in the treatment of the challenging infections caused by *Strenotrophomonas maltophilia,* tuberculosis and/or *Pseudomonas.*

In a particular embodiment, the combination therapy defined herein is used for the treatment of infections caused by *Strenotrophomonas maltophilia.*

In a particular embodiment, the combination therapy defined herein is used for the treatment of tuberculosis (e.g. mycobacterium tuberculosis).

In a particular embodiment, the combination therapy defined herein is used for the treatment of infections caused by *Pseudomonas.*

The compounds of Formula I are β-lactamase inhibitors. It will be appreciated that it may be desirable to administer one or more β-lactam antibiotics as part of combination therapy defined herein. In addition, or as an alternative, it may be desirable to administer more than one β-lactamase inhibitor as part of the combination therapy. For example, each β-lactamase inhibitor could inhibit a different spectrum of β-lactamase enzymes. In an embodiment, the compound of formula I may be administered in conjunction with a further β-lactamase inhibitor that inhibits L1 (or class B3 MBLs). This would be desirable for therapies with certain β-lactam antibacterial agents, such as meropenem, that are susceptible to breakdown by L1 (or class B3 MBL) metabolism.

The compounds of Formula I may be administered simultaneously or sequentially with the β-lactam antibiotic. In an embodiment, the administration is simultaneous. In another embodiment, the administration is sequential, e.g. the compound of Formula I may be administered before or after the administration of the β-lactam antibiotic.

Routes of Administration

The compounds of the present invention, or pharmaceutical compositions comprising these compounds, may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

EXAMPLES

Description of Drawings

Embodiments of the invention will be described, by way of example only, with reference to the accompanying drawings, in which.

Abbreviations

Figure 1:
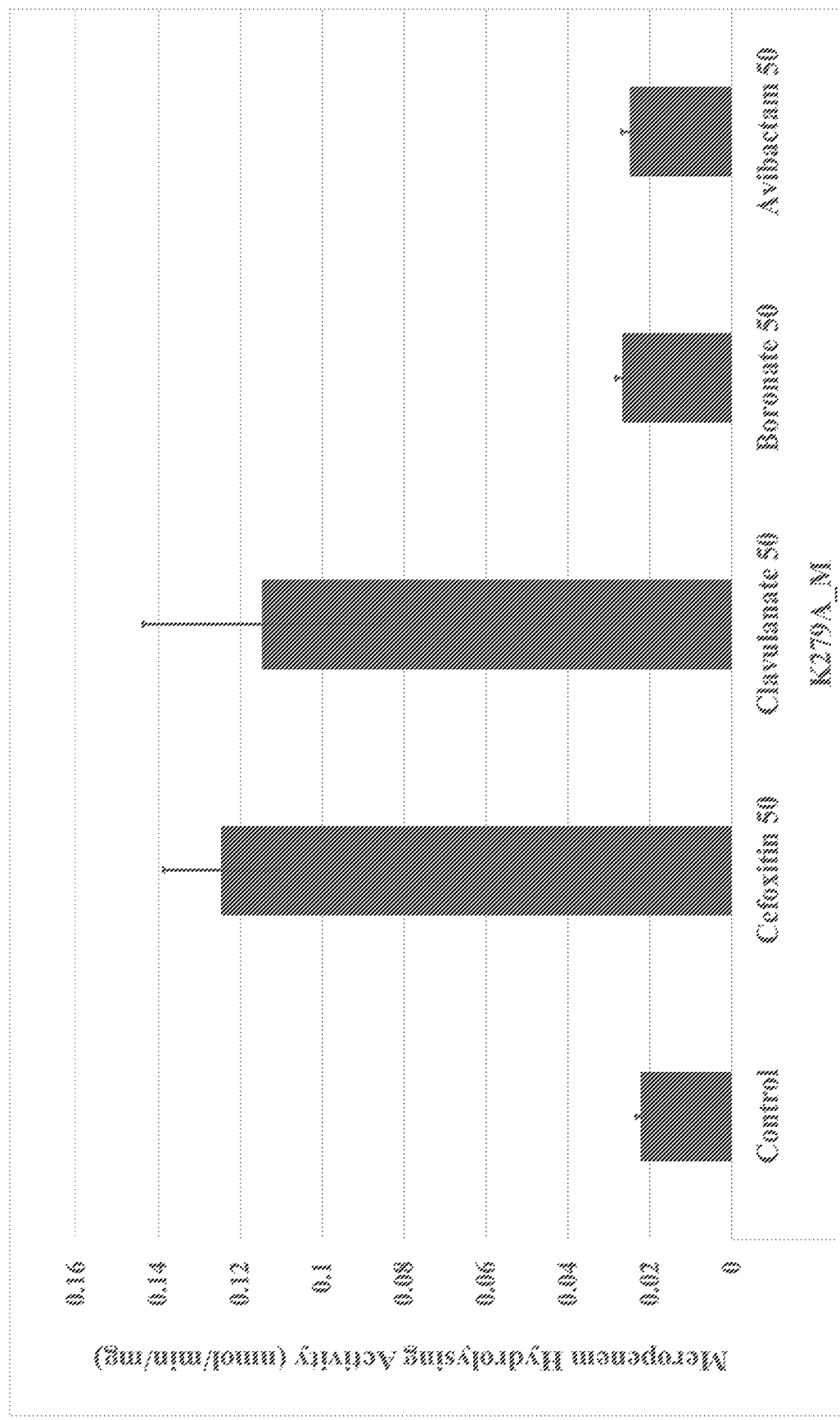
FIG. 1 shows the L1 β-lactamase induction by β-lactamase inhibitors in S. maltophilia K279a. K279a strain was incubated in presence of different inducers (50 μg.mL$^{-1}$ cefoxitin, 50 μg.mL$^{-1}$ clavulanate, 50 μg.mL$^{-1}$ boronate, 50 μg.mL$^{-1}$ avibactam, n=3). L1 activity was measured from the cell extracts in a 96-well plate reader by determining meropenem hydrolysis (100 μM) at λ=300 nm. Protein concentration was determined by using BioRad protein assay dye reagent. Specific activity was calculated by using the extinction coefficient of 9600 AU/M/cm and a pathlength correction for the microplate (0.62 mm). Data presented are means +/−SEM, n=3.

ATM Aztreonam
AVI Avibactam
BSA Bovine serum albumin
BOR cyclic boronate compound 2
CA Clavulanic acid
CAZ Ceftazidime
CLSI Clinical & Laboratory Standards Institute
DMSO dimethylsulfoxide
ESBL Extended-Spectrum beta-Lactamase
HEPES 4-(2-hydroxyethyl)-1-piperazineethanesulfonic acid
KPC-2 Klebsiella pneumoniae carbapenemase-2
FC5 The Hydroxylcoumarin Cephalosporin as shown in J Med Chem. 2013 Sep 12; 56(17): 6945-6953.
MBL metallo-β-lactamase
MIC minimum inhibitory concentration
PDB Protein Data Bank
PEG polyethylene glycol
PEG MME poly(ethylene glycol) monomethyl ether
SBL serine-β-lactamase
Tris. tris(hydroxymethyl)aminomethane

Bacterial Isolates and Materials

S. maltophilia clinical isolates were K279a, a well characterised isolate from Bristol, UK, or were obtained from the SENTRY antimicrobial resistance survey, as previously reported [51]. The ceftazidime resistant, β-lactamase hyper-producing mutant K CAZ 10 has previously been described [52]. Efflux-pump over producing mutants K AMI 32 and K MOX 8 were selected using K279a as parent strain as described previously [53]. All growth media were from Oxoid. Chemicals were from Sigma, unless otherwise stated. Avibactam and cyclic boronate 2 were synthesised according to published protocols [54].

Cyclic Boronates 1 and 2

The use of the term "cyclic boronate 1" (or simply "1") and the term "cyclic boronate 2" (or simply "2") in the following illustrative examples refers to the following compounds:

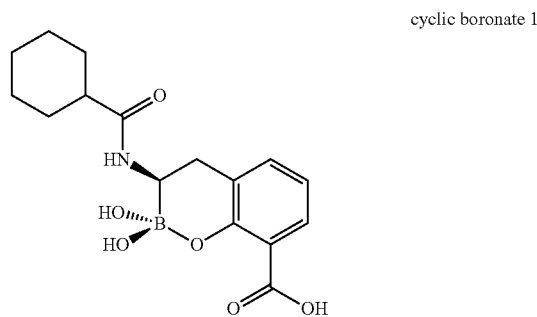

cyclic boronate 1

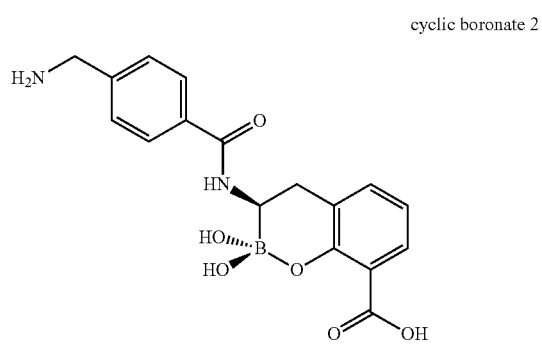

cyclic boronate 2

Assay Of β-Lactamase Activity in Cell Extracts, β-Lactamase Induction and β-Lactam Susceptibility Cultures were grown overnight using nutrient broth and used to inoculate (1:100 dilution) 10 ml nutrient broth cultures in sealed 30 ml universal bottles. Cultures were incubated for 2 h with shaking at 37° C. before test inducers were added, or not, and culture was continued for 2 h. Cells were pelleted by centrifugation (4,000×g, 10 min) and pellets treated with 100 μL of BugBuster (Ambion), pipetting up and down a few times before rocking for 10 min at room temperature. Cell debris and unlysed cells were pelleted by centrifugation (13,000×g, 5 min) and the supernatant retained as a source of crude cell protein. Protein concentration was determined using the BioRad protein assay reagent concentrate according to the manufacturer's instructions. L1 β-lactamase activity was determined using an Omega Fluostar (BMG Biotech) using meropenem as substrate in half-area 96 well UV-translucent plates (Greiner UV-Star. Bio-one) with 200 μl of 100 μM meropenem solution in assay buffer (60 mM $Na_2HPO_4.7H_2O$ pH 7.0, 40 mM $NaH_2PO_4.H_2O$, 10 mM KCl, 1 mM $MgSO_4.7H_2O$, 100 μM $ZnCl_2$) plus 10 μL of cell extract. Substrate depletion was followed at 300 nm for 10 mins and an extinction coefficient of 9600 AU/M was used to calculate enzyme activity in the linear phase of the reaction.

Susceptibility to β-lactams in bacterial isolates was determined using the CLSI microtitre minimum inhibitory concentration (MIC) methodology with Muller-Hinton Broth using 96 well plates (Corning, Costar). The MIC was determined as the lowest concentration of β-lactam required to entirely suppress growth [55]. Inhibitor concentrations were kept constant at 2 mg/L or 10 mg/L in all assays. Interpretation of susceptibility/resistance was by reference to CLSI clinical breakpoints for *S. maltophilia* (ceftazidime) and for Pseudomonas aeruginosa (for aztreonam and meropenem, since no *S. maltophilia* breakpoints are available) [56].

Purification of L1 and L2 Proteins

Recombinant L1 and L2 protein were produced in Escherichia coli and purified as previously described. Enzyme activity was monitored using an Omega Fluorostar (BMG Labtech) using buffer L1 (50 mM HEPES pH 7.5, 10 μg/mL BSA, 10 μM $ZnSO_4$ and 0.01% v/v Triton 100) and buffer L2 (50 Mm Tris pH 7.5, 10 μg/mL BSA and 0.01% v/v Triton 100. For the chromogenic substrates meropenem, ceftazidime and aztreonam, substrate depletion was measured at 300 nm, 260 nm, 318 nm, respectively whilst for the fluorogenic substrate FC5, the excitation wavelength was set at 380 nm and emission wavelength at 460 nm [57]. Clavulanic acid was dissolved in double distilled water while avibactam and cyclic boronate 2 were dissolved in DMSO to prepare an appropriate stock solution. Steady state kinetic data were analysed by curve fitting to the Michaeilis-Menten equation using Prism software.

Cyclic Boronate Compound 2 Restores Aztreonam Activity but Not Meropenem Activity Against *S. Maltophilia*

As a prelude to investigation the effects of β-lactamase inhibitors, the hydrolysis of a range of candidate β-lactams in vitro by purified L1 (class B3 MBL) and L2 (class A ESBL) under steady state conditions were investigated. The results (Table 1) showed the carbapenem meropenem to be predominantly a substrate for L1, with L2 showing only weak hydrolytic activity, the monobactam aztreonam to be a substrate for L2 only and both L1 and L2 to hydrolyse the oxyamino-cephalosporin with similar efficiencies.

TABLE 1

Kinetic data for β-lactams tested against *S. maltophilia* β-lactamases

| Enzyme | Substrate | [E] (μM) | $K_M$ (μM) | $k_{cat}$ ($s^{-1}$) | $k_{cat}/K_M$ ($\mu M^{-1} \cdot s^{-1}$) × $10^{-3}$ |
|---|---|---|---|---|---|
| L1 | CAZ | 0.5 | 259.5 | 1.67 | 6.4 |
|    | ATM | 0.5 | — | — | — |
|    | Meropenem | 10 | 105 | 23.8 | 227 |
|    | FC5 | 0.05 | 29.6 | 146 | 4,932 |
| L2 | CAZ | 0.5 | 548.5 | 1.88 | 3.4 |
|    | ATM | 0.5 | 119.4 | 0.08 | 0.67 |
|    | Meropenem | 0.625 | 28.83 | 0.028 | 0.97 |
|    | FC5 | 0.05 | 17.9 | 208.6 | 11,653 |

Next, the ability of three β-lactamase inhibitors: clavulanic acid, avibactam and cyclic boronate 2 (each at 2 mg/L) to potentiate the activity of the target β-lactams against S. maltophilia was tested. All three inhibitors could reverse aztreonam but not meropenem resistance in ceftazidime susceptible clinical isolates (K279a, CI-20, CI-29). Furthermore, all three inhibitors reversed ceftazidime and aztreonam but not meropenem resistance in a ceftazidime-resistant L1/L2 hyper-producing mutant (K CAZ 10), derived from K279a. However, all three inhibitors failed to restore ceftazidime susceptibility in a ceftazidime resistant L1/L2 hyper-producing clinical isolate (CI-31). Importantly, there is no general block on inhibitor activity in CI-31, as all three inhibitors could reverse aztreonam resistance in this strain (Table 2).

Outer membrane efflux pumps play a major role in antimicrobial resistance in *S. maltophilia*. Thus, to investigate the possible effect of multi-drug efflux pumps on β-lactamase inhibitor efficacy, we selected two hyper-resistant mutants from the isolate K279a using antibiotics known to be efflux pump substrates. Comparative proteomics confirmed that the two mutants, K MOX 8 and K AMI 32, hyper-produce the SmeDEF and SmeYZ efflux pumps, respectively. In K MOX 8, SmeYZ was downregulated as SmeDEF was hyperproduced, as expected given their reciprocal regulation [53]. All three β-lactamase inhibitors retained full activity against these efflux pump hyperproducing mutants (Table 2) ruling out efflux as a contributing factor to the observed variation in efficacy of the various β-lactam inhibitor combinations.

TABLE 2

Inhibition of *S. maltophilia* by ceftazidime, aztreonam and meropenem in the presense of β-lactamase inhibitors clavulanic acid, avibactam and cyclic boronate compound 1

|  | Ceftazidime | | | | Aztreonam | | | | Meropenem | | | |
|---|---|---|---|---|---|---|---|---|---|---|---|---|
|  | – | +CLA | +BOR | +AVI | – | +CLA | +BOR | +AVI | – | +CLA | +BOR | +AVI |
| K279a | 4 | 4 | 0.5 | 1 | 128 | 1 | 1 | 1 | 8 | 32 | 4 | 16 |
| CI-20 | 16 | 16 | 2 | 4 | 128 | 4 | 2 | 2 | 64 | 32 | 8 | 64 |
| CI-29 | 8 | 4 | 0.5 | 1 | 128 | 1 | 1 | 1 | 32 | 16 | 8 | 32 |
| K CAZ 10 | 64 | 8 | 4 | 8 | 256 | 0.5 | 1 | 1 | 64 | 8 | 16 | 64 |
| CI-31 | 256 | 128 | 128 | 128 | 256 | 2 | 4 | 4 | 256 | 256 | 256 | 256 |
| K AMI 32 | 2 | 1 | 1 | 0.5 | 128 | 0.5 | 1 | 0.5 | 4 | 8 | 4 | 16 |
| K MOX 8 | 4 | 1 | 0.5 | 0.5 | 128 | 0.25 | 1 | 0.5 | 4 | 8 | 8 | 16 |

Shaded values represent resistance.

Inhibition of the *S. maltophilia* L1 MBL

On the basis of these in vitro data we conclude that the bicyclic boronate 2 acts against *S. maltophilia* in a similar fashion to avibactam and clavulanic acid in its ability to reverse aztreonam and (when due to L1/L2 hyperproduction) ceftazidime resistance (Table 2). As to date the inhibition of class B3 MBLs by bicyclic boronates has not been reported, we investigated the inhibition of purified L1 and L2 by the three inhibitors using the fluorogenic β-lactamase substrate FC5 as a reporter. Steady-state $kcat/K_M$ values clearly demonstrate that FC5 is hydrolysed with high efficiency by both L1 and L2 (Table 1). IC50 measurements revealed that while all three compounds inhibit L2 with nanomolar potencies (Table 5), no inhibition of L1 was observed for any of the three inhibitors, even when using inhibitor concentrations up to 2.5 mM.

TABLE 5

Inhibition of L2 by β-lactamase inhibitors in vitro.

| Inhibitor | $IC_{50}$ (nM) | $pIC_{50}$ |
|---|---|---|
| Clavulanic acid | 22.3 | 7.41 |
| Avibactam | 14.36 | 7.84 |
| Boronate 2 | 5.25 | 8.27 |

Structural Basis for Inhibition of L2 by Avibactam and the Bicyclic Boronate 2

The results above demonstrate that, consistent with the effectiveness of β-lactam combinations against *S. maltophilia* strains, L2 is effectively inhibited by both avibactam and the bicyclic boronate 2. To understand the molecular basis for this inhibition we crystallised L2 and soaked the crystals in avibactam or bicyclic boronate 2. Consistent with our inhibition kinetics data, we were unable to obtain crystal structures of L1 with these inhibitors. L2 crystallised in the space group $P2_12_12_1$ with two molecules in the asymmetric unit, and conserves the overall SBL fold with, for example, an RMSD to KPC-2 (PDB 2OV5) of 0.2 Å.

L2:avibactam and L2:cyclic boronate 2 co-complex structures were solved to 1.35 Å and 2.09 Å resolution, respectively, with clear $F_o$-$F_c$ density indicating both inhibitors form a covalent attachment to the active site nucleophile Ser70. Binding by both compounds reveals no significant changes in the L2 active site in comparison with apo or D-glutamate structures. Indeed, the catalytic water in both is positioned similarly to native and D-glutamate-bound structures.

Cyclic boronate 2 binds L2 with the boron atom in a tetrahedral geometry, as observed previously on binding to CTX-M-15 (another class A ESBL) [21] and OXA-10 (a class D SBL) [9], mimicking the tetrahedral intermediate formed during β-lactam hydrolysis. As in D-glutamate binding, the OH group on the boron atom is positioned to interact with the backbone amides of Ser70 (2.95 Å) and Ser237 (3.1 Å) in the oxyanion hole. Cyclic boronate 2 makes additional hydrogen bonds with side chain atoms of residues Ser130 (2.77 Å to the bicyclic ring oxygen), Asn132 (3.0 Å to the acetamide oxygen), Ser237 (2.96 Å to the carboxylate) Thr235 (2.65 Å to the carboxylate), and the backbone carbonyl oxygen of Ser237 (3.1 Å to the acetamide nitrogen). In addition, binding is stabilised by significant hydrophobic interactions with His105.

β-Lactamase Production is Not Induced by Avibactam and Cyclic Boronate 2

Figure 2A:
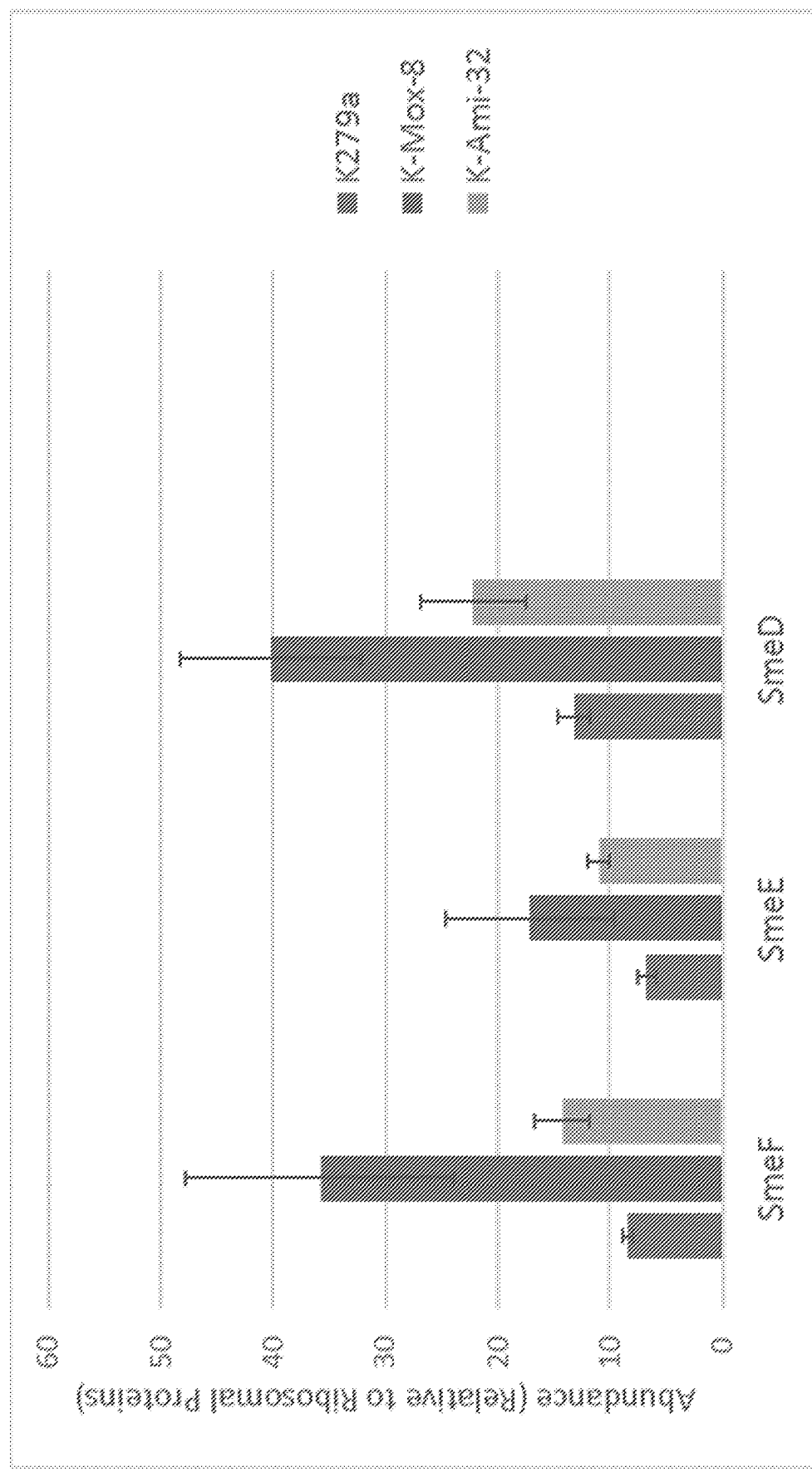
FIG. 2 (A and B) shows the efflux pump production in S. maltophilia mutants. Protein abundance data (relative to average ribosomal abundance) is reported as mean +/−Standard Error of the Mean (n=3).
Figure 2B:
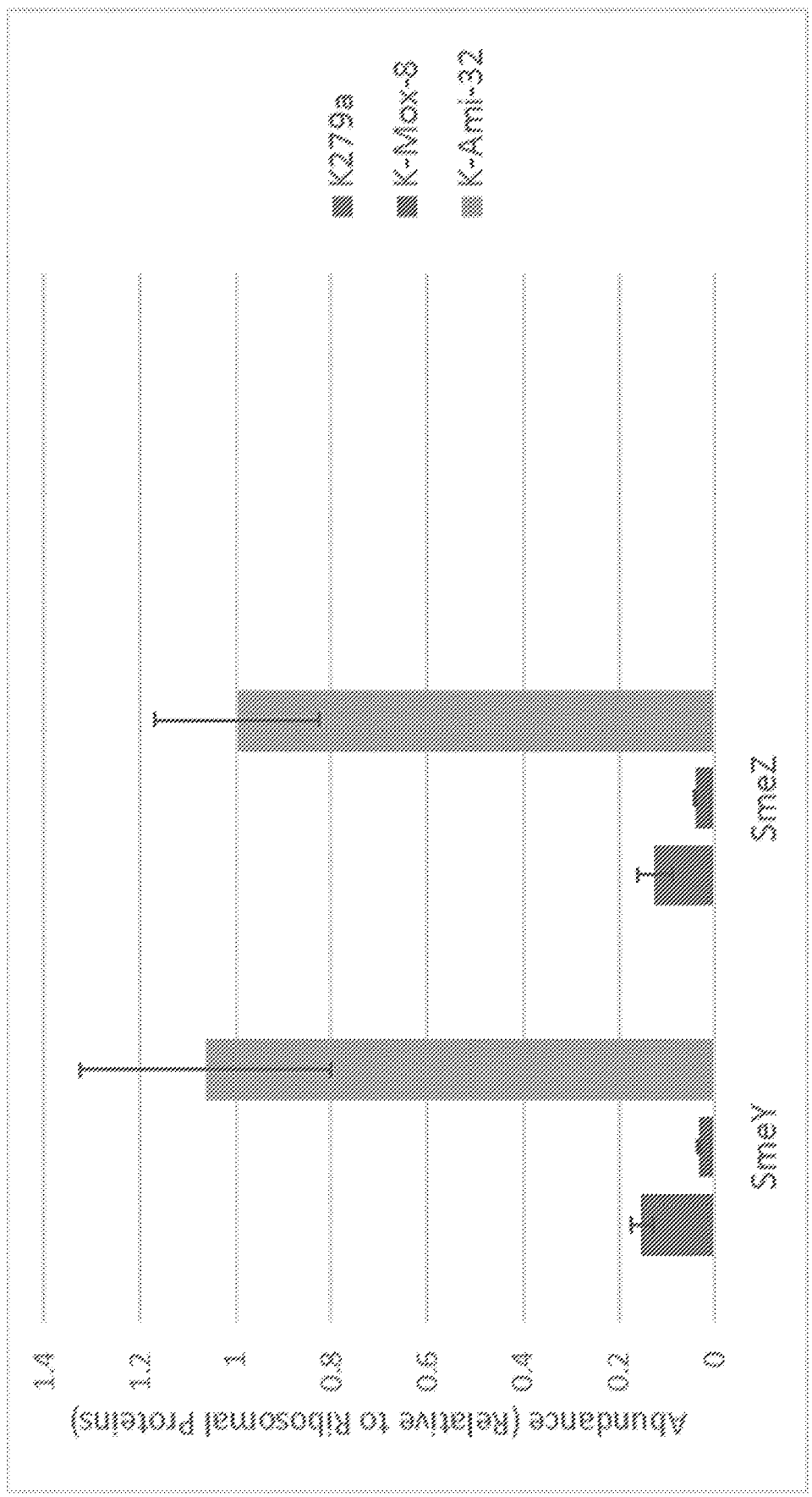

One important consideration when deploying β-lactamase inhibitors into clinical practice is that some can interact with penicillin binding proteins and trigger β-lactamase induction pathways carried by many bacteria. L1 and L2 production in *S. maltophila* is controlled by a transcriptional regulator, AmpR, which is responsive to β-lactam challenge via sensing β-lactam mediated perturbations in peptidoglycan breakdown and recycling. Clavulanic acid induced L1 production (measured using meropenem hydrolysis in cell extracts) very similarly to the positive control β-lactam cefoxitin in *S. maltophilia* wild type strain K279a (FIG. 2). This explains why clavulanic acid does not reduce the MIC of ceftazidime against *S. maltophilia* K279a (Table 2): induction of L1 by clavulanic acid overcomes inhibition of L2 by clavulanic acid (Table 5) because L1 can hydrolyse ceftazidime (Table 1). Since L1 does not hydrolyse aztreonam (Table 1), however, clavulanic acid reduces the aztreonam MIC against K279a, in spite of its ability to induce L1 production (Table 2). Unlike clavulanic acid, avibactam and cyclic boronate 2 reduce ceftazidime MICs against K279a (Table 2). This observation is explained by our key finding that neither avibactam nor 2 induces L1 to any measurable extent (FIG. 2) and yet both inhibit L2 (Table 5).

Figure 3:
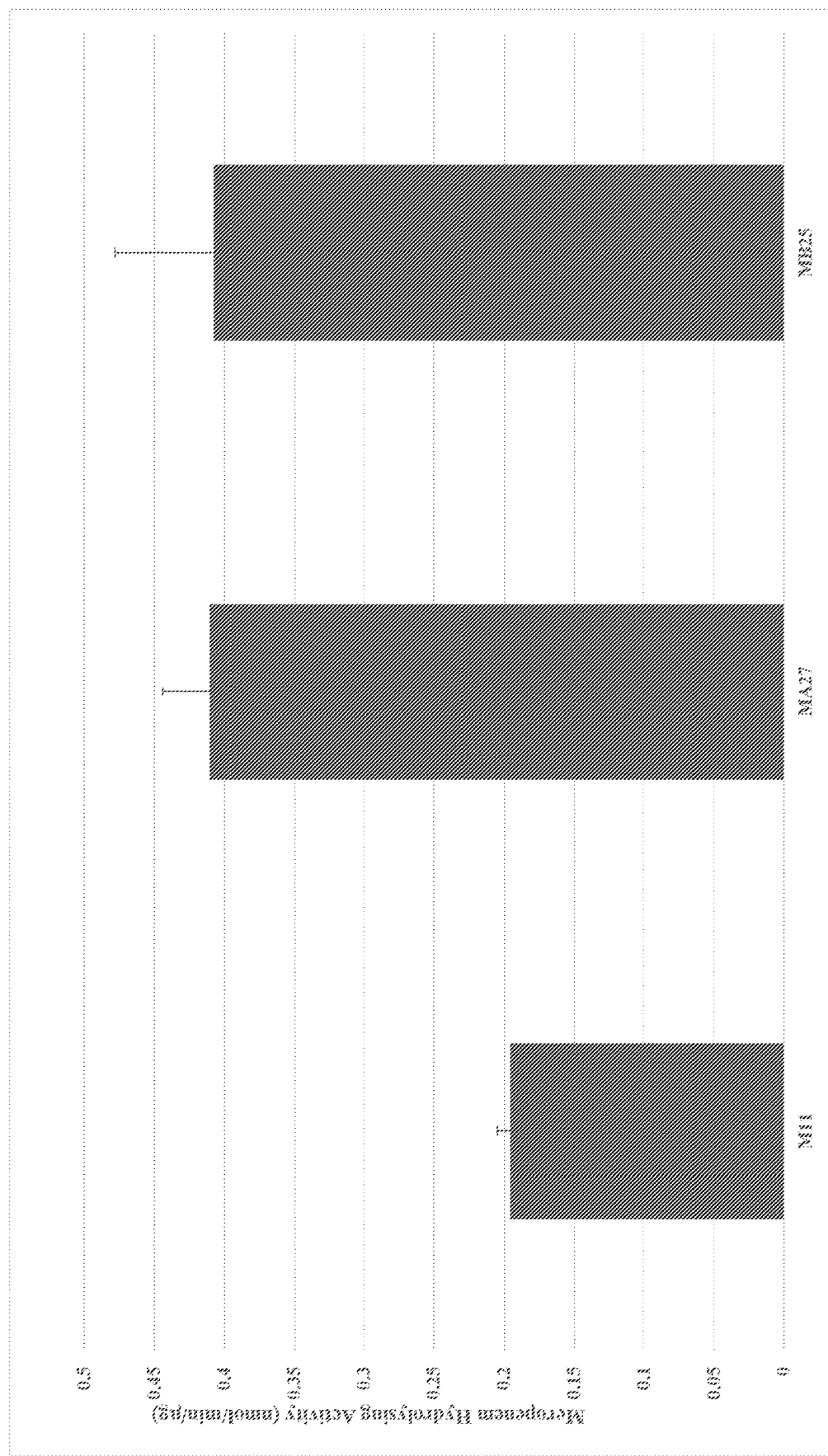
FIG. 3 shows the L1 activity of derivatives from a L1 and L2 hyper-producer strain. Meropenem hydrolysis for selected mutants increases (MA27 and MB25), doubles the original activity of M11. Ceftazidime/avibactam originated MA27 whilst ceftazidime/2, MB25.

Even though our structural and kinetic work confirmed L2 is potently inhibited by avibactam and 2, we predicted failure of avibactam/ceftazidime against *S. maltophilia*. This is because mutants that hyperproduce L1 are readily obtained from *S. maitophilia* isolates, and avibactam does not inhibit MBLs. Whilst 2 inhibits class B1 MBLs, this work revealed that it does not inhibit the class B3 MBL, L1 (Table 3) and so 2/ceftazidime was also overcome by L1 hyperproduction (FIG. 3). It may be possible to modify 2 and so generate a broader-spectrum MBL inhibitor. However, a key finding of this work is that such a modification might not be necessary. Avibactam and 2 both facilitate killing of *S. maltophilia* when paired with the monobactam, aztreonam, reducing MICs to ≤4 mg/L even in the pan-resistant clinical *S. maltophilia* isolate, CI-31 (Table 2). This implies that aztreonam/avibactam and aztreonam/2 may have a promising clinical future for treatment of infections caused by this most intractable of species. The fact that efflux pump overproduction does not affect aztreonam/2 or aztreonam/avibactam activity (Table 2) gives even greater cause for optimism. We were interested to read, therefore, a recent clinical case report demonstrating the use of combination therapy with ceftazidime/avibactam plus aztreonam to save the life of a patient with an *S. maltophilia* infection that had failed all prior therapy. Our structural, kinetic and whole bacterial killing data would lead to the conclusion that ceftazidime was probably superfluous in this success, but our work indicates that ceftazidime/avibactam plus aztreonam might be routinely considered in the clinic for use against seemingly untreatable *S. maltophilia* infections.

Inhibition of Mycobacterium Tuberculosis BlaC

BlaC Production

Recombinant BlaC, with an N-terminal His-tag, was produced in *E. coli* BL21(DE3) cells using auto-induction medium supplemented with 50 μg mL$^{-1}$ ampicillin. Cells were grown for four hours at 37° C. before cooling to 18° C. and continuing growth overnight. Cells were harvested by centrifugation (10 min, 10000 g).

20 g of BlaC cell pellet were resuspended in 100 mL HisTrap Buffer A (50 mM HEPES, pH 7.5, 500 mM NaCl, 5 mM imidazole) supplemented with DNAse I and PMSF (2 g$^{-1}$ final concentration), and lysed by sonication using a Vibra-Cell sonicator (SONICS, 10 min, 60% amplitude, 10 s pulse, 10 s rest). The supernatant was loaded onto a 5 mL HisTrap HP column (GE Healthcare Life Sciences) followed by extensive washing with HisTrap Buffer A before elution with a gradient of HisTrap Buffer B in HisTrap Buffer A (20-500 mM imidazole). Fractions containing purified enzyme were concentrated by centrifugal ultrafiltration using an Amicon Ultra 15 mL centricon with a 10 kDa molecular weight cut off (Millipore). The resultant solution was injected onto a Superdex S200 column (300 mL), pre-equilibrated with Gel Filtration Buffer (50 mM HEPES, ph 7.5, 500 mM NaCl), and eluted with an additional 300 mL of Gel Filtration Buffer. Fractions containing pure HisTagged enzyme were incubated overnight at 4° C. with HisTagged 3C protease (1:100 w/w) to remove the N-terminal HisTag. The 3C protease together with any uncleaved protein was removed from the digestion mixture with a second 5 mL HisTrap HP column, pre-equilibrated with HisTrap Wash Buffer (50 mM HEPES, pH 7.5, 500 mM NaCl, 20 mM imidazole). Purified enzyme fractions, identified by SDS-PAGE analysis, were collected and concentrated by centrifugal ultrafiltration before buffer exchange into Exchange Buffer (25 mM HEPES, pH 7.5, 100 mM NaCl).

FC5 Steady-State Kinetic Assays

FC5 was stored as a 2.5 mM solution in assay buffer supplemented with 10% (v/v) DMSO. Fluorescence measurements were made using a PHERAstar multi-mode plate reader (BMG Labtech). All assays were carried out at 25° C. Fluorescence assays were carried out using black 96 well format half area clear® plates (Greiner Bio-One) with a final assay volume of 100 µL. FC5 hydrolysis was followed by fluorescence ($\lambda_{ex}$=380 nm, $\lambda_{em}$=460 nm) corresponding to the release of the umbelliferone fluorophore. The optimum concentration of enzyme for steady-state measurements was determined by examining the rate of substrate hydrolysis at varied concentrations of enzyme, with the concentration at which the initial rate remained constant for 5-10 min being selected as an appropriate enzyme concentration. Initial rates of substrate hydrolysis were determined at varying substrate concentrations. Steady-state kinetic parameters were determined by fitting of initial rates to the Michaelis-Menten equation using GraphPad Prism 5 software.

Inhibition Assays

Inhibition assays were performed by monitoring the initial rate of FC5 hydrolysis via fluorescence at a range of inhibitor concentrations. Inhibitors were stored either as solids or as 100 mM stock solutions in DMSO, these were diluted to appropriate concentrations in the assay buffer. Typically inhibition assays were carried out using black 384 well format pclear® plates (Griener Bio-One) with a final assay volume of 25 µL. Enzyme concentrations were chosen to give a linear rate of FC5 hydrolysis over the first 5 min of the assay time with an FC5 concentration of 5 µM. Components were added in the following order and volumes:

| Reagent | Inhibited Enzyme Volume (µL) | Free Enzyme Volume (µL) | Background Hydrolysis Volume (µL) |
|---|---|---|---|
| Inhibitor Solution | 1 | — | — |
| Assay Buffer | 14 | 15 | 20 |
| 5X Enzyme Solution | 5 | 5 | — |
| 25 µM FC5 | 5 | 5 | 5 |

The enzyme was incubated with the inhibitor for 10 min prior to initiation of the reaction by the addition of the substrate. The residual activities were calculated using the following formula:

$$\%RA = \frac{100 \times (V_{inhibited} - V_{background})}{(V_{uninhibited} - V_{background})}.$$

$IC_{50}$ values were calculated by fitting of residual residual activity curves using GraphPad Prism 5 software.

TABLE 9

BlaC IC50 values for various β-lactamase inhibitors

| Compound | Pre-incubation Time/min | $pIC_{50}$ |
|---|---|---|
| Clavulanate | 0 | 5.39 ± 0.05 |
| | 10 | 6.20 ± 0.03 |
| | 60 | 6.58 ± 0.04 |
| Sulbactam | 0 | 5.86 ± 0.02 |
| | 10 | 5.92 ± 0.02 |
| | 60 | 5.76 ± 0.02 |
| Tazobactam | 0 | 5.19 ± 0.03 |
| | 10 | 5.56 ± 0.06 |
| | 60 | 5.45 ± 0.02 |
| Avibactam | 0 | <4 |
| | 10 | 4.84 ± 0.05 |
| | 60 | 5.85 ± 0.04 |
| BLI-489 | 0 | 6.15 ± 0.07 |
| | 10 | 6.57 ± 0.03 |
| | 60 | 6.71 ± 0.06 |
| Imipenem | 0 | 5.59 ± 0.01 |
| | 10 | 6.09 ± 0.02 |
| | 60 | 6.45 ± 0.05 |
| Faropenem | 0 | 5.43 ± 0.02 |
| | 10 | 5.60 ± 0.04 |
| | 60 | 5.45 ± 0.03 |
| Meropenem | 0 | 5.72 ± 0.06 |
| | 10 | 6.41 ± 0.05 |
| | 60 | 7.16 ± 0.03 |
| 1 | 0 | 6.83 ± 0.01 |
| | 10 | 6.8 ± 0.1 |
| | 60 | 6.94 ± 0.01 |
| 2 | 0 | 7.63 ± 0.08 |
| | 10 | 8 |
| | 60 | >8 |

While specific embodiments of the invention have been described for the purpose of reference and illustration, various modifications will be apparent to a person skilled in the art without departing from the scope of the invention as defined by the appended claims.

REFERENCES

1. Hamad, B., The antibiotics market. Nat Rev Drug Discov, 2010. 9(9): p. 675-676.

2. Van Boeckel, T.P., et al., Global antibiotic consumption 2000 to 2010: an analysis of national pharmaceutical sales data. The Lancet Infectious Diseases. 14(8): p. 742-750.

3. Versporten, A., et al., Antibiotic use in eastern Europe: a cross-national database study in coordination with the WHO Regional Office for Europe. Lancet Infectious Diseases, 2014. 14(5): p. 381-387.

4. Strynadka, N.C.J., et al., Molecular structure of the acyl-enzyme intermediate in [beta]-lactam hydrolysis at 1.7 A resolution. Nature, 1992. 359(6397): p. 700-705.

5. Drawz, S.M. and R.A. Bonomo, Three Decades of β-Lactamase Inhibitors. Clinical Microbiology Reviews, 2010. 23(1): p. 160-201.

6. Ambler, R.P., The Structure of &It;latex&gt; $\beta$&It;/latex&gt;-Lactamases. Philosophical Transactions of the Royal Society of London. B, Biological Sciences, 1980. 289(1036): p. 321.

7. Bush, K., The ABCD's of β-lactamase nomenclature. Journal of Infection and Chemotherapy, 2013. 19(4): p. 549-559.

8. King, A.M., et al., Structural and Kinetic Characterization of Diazabicyclooctanes as Dual Inhibitors of Both Serine-β-Lactamases and Penicillin-Binding Proteins. ACS Chemical Biology, 2016. 11(4): p. 864-868.

9. Brem, J., et al., Structural basis of metallo-beta-lactamase, serine-beta-lactamase and penicillin-binding protein inhibition by cyclic boronates. Nature Communications, 2016. 7.

10. Drawz, S.M., K.M. Papp-Wallace, and R.A. Bonomo, New beta-Lactamase Inhibitors: a Therapeutic Renaissance in an MDR World. Antimicrobial Agents and Chemotherapy, 2014. 58(4): p. 1835-1846.

11. Al Roomi, L.G., et al., Amoxycillin and clavulanic acid in the treatment of urinary infection. Archives of Disease in Childhood, 1984. 59(3): p. 256-259.

12. Reading, C. and M. Cole, Clavulanic Acid: a Beta-Lactamase-Inhibiting Beta-Lactam from Streptomyces clavuligerus. Antimicrobial Agents and Chemotherapy, 1977. 11(5): p. 852-857.

13. Fass, R.J. and R.B. Prior, Comparative in vitro activities of piperacillin-tazobactam and ticarcillin-clavulanate. Antimicrobial Agents and Chemotherapy, 1989. 33(8): p. 1268-1274.

14. Finlay, J., L. Miller, and J.A. Poupard, A review of the antimicrobial activity of clavulanate. Journal of Antimicrobial Chemotherapy, 2003. 52(1): p. 18-23.

15. Sulton, D., et al., Clavulanic acid inactivation of SHV-1 and the inhibitor-resistant 5130G SHV-1 beta-lactamase—Insights into the mechanism of inhibition. Journal of Biological Chemistry, 2005. 280(42): p. 35528-35536.

16. Stachyra, T., et al., Mechanistic studies of the inactivation of TEM-1 and P99 by NXL104, a novel non-beta-lactam beta-lactamase inhibitor. Antimicrob Agents Chemother, 2010. 54(12): p. 5132-8.

17. Coleman, K., Diazabicyclooctanes (DBOs): a potent new class of non-β-lactam β-lactamase inhibitors. Current Opinion in Microbiology, 2011. 14(5): p. 550-555.

18. Wang, D.Y., et al., The road to avibactam: the first clinically useful non-beta-lactam working somewhat like a beta-lactam. Future Medicinal Chemistry, 2016. 8(10): p. 1063-1084.

19. Abboud, M.I., et al., Interaction of Avibactam with Class B Metallo-beta-Lactamases. Antimicrobial Agents and Chemotherapy, 2016. 60(10): p. 5655-5662.

20. Hecker, S.J., et al., Discovery of a Cyclic Boronic Acid β-Lactamase Inhibitor (RPX7009) with Utility vs Class A Serine Carbapenemases. Journal of Medicinal Chemistry, 2015. 58(9): p. 3682-3692.

21. Cahill, S.T., et al., Cyclic Boronates Inhibit All Classes of beta-Lactamase. Antimicrob Agents Chemother, 2017.

22. Ryan, R.P., et al., The versatility and adaptation of bacteria from the genus Stenotrophomonas. Nat Rev Micro, 2009. 7(7): p. 514-525.

23. Brooke, J.S., Stenotrophomonas maltophilia: an Emerging Global Opportunistic Pathogen. Clinical Microbiology Reviews, 2012. 25(1): p. 2-41.

24. de Vrankrijker, A.M.M., T.F. W. Wolfs, and C.K. van der Ent, Challenging and emerging pathogens in cystic fibrosis. Paediatric Respiratory Reviews, 2010. 11(4): p. 246-254.

25. Alonso, A. and J.L. Martinez, Cloning and characterization of SmeDEF, a novel multidrug efflux pump from Stenotrophomonas maltophilia. Antimicrob Agents Chemother, 2000. 44(11): p. 3079-86.

26. Gould, V.C. and M.B. Avison, SmeDEF-mediated antimicrobial drug resistance in Stenotrophomonas maltophilia clinical isolates having defined phylogenetic relationships. J Antimicrob Chemother, 2006. 57(6): p. 1070-6.

27. Garcia-Leon, G., et al., High-level quinolone resistance is associated with the overexpression of smeVWX in Stenotrophomonas maltophilia clinical isolates. Clinical Microbiology and Infection, 2015. 21(5): p. 464-467.

28. Gould, V.C., A. Okazaki, and M.B. Avison, Coordinate hyperproduction of SmeZ and SmeJK efflux pumps extends drug resistance in Stenotrophomonas maltophilia. Antimicrob Agents Chemother, 2013. 57(1): p. 655-7.

29. Walsh, T.R., et al., Sequence-Analysis of the L1 Metallo-Beta-Lactamase from Xanthomonas-Maltophilia. Biochimica Et Biophysica Acta-Gene Structure and Expression, 1994. 1218(2): p. 199-201.

30. Walsh, T.R., A.P. MacGowan, and P.M. Bennett, Sequence analysis and enzyme kinetics of the L2 serine beta-lactamase from Stenotrophomonas maltophilia. Antimicrobial Agents and Chemotherapy, 1997. 41(7): p. 1460-1464.

31. Gould, V.C., A. Okazaki, and M.B. Avison, Beta-lactam resistance and beta-lactamase expression in clinical Stenotrophomonas maltophilia isolates having defined phylogenetic relationships. J Antimicrob Chemother, 2006. 57(2): p. 199-203.

32. Lemmen, S. W, et al., Comparison of serum bactericidal activity of ceftazidime, ciprofloxacin and meropenem against Stenotrophomonas maltophilia. Journal of Antimicrobial Chemotherapy, 2001. 47(1): p. 118-120.

33. Okazaki, A. and M.B. Avison, Induction of L1 and L2 beta-lactamase production in Stenotrophomonas maltophilia is dependent on an AmpR-type regulator. Antimicrob Agents Chemother, 2008. 52(4): p. 1525-8.

34. Talfan, A., et al., Involvement of mutation in ampD I, mrcA, and at least one additional gene in beta-lactamase hyperproduction in Stenotrophomonas maltophilia. Antimicrob Agents Chemother, 2013. 57(11): p. 5486-91.

35. Hanes, M.S., et al., Structural and Biochemical Characterization of the Interaction between KPC-2 β-Lactamase and β-Lactamase Inhibitor Protein. Biochemistry, 2009. 48(39): p. 9185-9193.

36. Krishnan, N.P., et al., Inhibition of Klebsiella beta-Lactamases (SHV-1 and KPC-2) by Avibactam: A Structural Study. Plos One, 2015. 10(9).

37. King, D.T., et al., Molecular Mechanism of Avibactam-Mediated beta-Lactamase Inhibition. Acs Infectious Diseases, 2015. 1(4): p. 175-184.

38. Lahiri, S.D., et al., Molecular Basis of Selective Inhibition and Slow Reversibility of Avibactam against Class D Carbapenemases: A Structure-Guided Study of OXA-24 and OXA-48. Acs Chemical Biology, 2015. 10(2): p. 591-600.

39. Xu, H., S. Hazra, and J.S. Blanchard, NXL104 Irreversibly Inhibits the beta-Lactamase from Mycobacterium tuberculosis. Biochemistry, 2012. 51(22): p. 4551-4557.

40. Lahiri, S.D., et al., Structural Insight into Potent Broad-Spectrum Inhibition with Reversible Recyclization Mechanism: Avibactam in Complex with CTX-M-15 and Pseudomonas aeruginosa AmpC beta-Lactamases. Antimicrobial Agents and Chemotherapy, 2013. 57(6): p. 2496-2505.

41. Lahiri, S.D., et al., Avibactam and Class C beta-Lactamases: Mechanism of Inhibition, Conservation of the Binding Pocket, and Implications for Resistance. Antimicrobial Agents and Chemotherapy, 2014. 58(10): p. 5704-5713.

42. Gorrec, F., The MORPHEUS protein crystallization screen. Journal of Applied Crystallography, 2009. 42(6): p. 1035-1042.

43. Kabsch, W, XDS. Acta Crystallographica Section D, 2010. 66(2): p. 125-132.

44. Waterman, D.G., et al., Diffraction-geometry refinement in the DIALS framework. Acta Crystallographica Section D, 2016. 72(4): p. 558-575.

45. Winn, M.D., et al., Overview of the CCP4 suite and current developments. Acta Crystallographica Section D: Biological Crystallography, 2011. 67(Pt 4): p. 235-242.

46. McCoy, A.J., et al., Phaser crystallographic software. Journal of Applied Crystallography, 2007. 40(4): p. 658-674.

47. Moriarty, N.W., R.W. Grosse-Kunstleve, and P.D. Adams, electronic Ligand Builder and Optimization Workbench (eLBOW) a tool for ligand coordinate and restraint generation. Acta Crystallographica Section D, 2009. 65(10): p. 1074-1080.

48. Emsley, P., et al., Features and development of Coot. Acta Crystallographica Section D, 2010. 66(4): p. 486-501.

49. Adams, P.D., et al., PHENIX: a comprehensive Python-based system for macromolecular structure solution. Acta Crystallographica Section D, 2010. 66(2): p. 213-221.

50. Chen, V.B., et al., MolProbity: all-atom structure validation for macromolecular crystallography. Acta Crystallographica Section D, 2010. 66(1): p. 12-21.

51. Avison M. B. et al., A TEM-2 β-lactamase encoded on an active Tn1-like transposon in the genome of a clinical isolate of Stenotrophomonas maltophilia, J. Antimicrob. Chemother. 2000, 46, 879-884.

52. Talfan A. et al., Involvement of mutation in ampD I, mrcA, and at least one additional gene in β-lactamase hyperproduction in Stenotrophomonas maltophilia, Antimicrob. Agents Chemother., 2013. 57(11): p. 5486-91.

53. Huang Y. W. et al., Overexpression of SmeDEF Efflux Pump Decreases Aminoglycoside Resistance in Stenotrophomonas maltophilia, Antimicrob. Agents Chemother., 2017, 61(5), pii: e02685-16.

54. Brem J. et al., Structural basis of metallo-β-lactamase, serine-β-lactamase and penicillin-binding protein inhibition by cyclic boronates, Nature Communications 7, Article number: 12406 (2016), doi:10.1038/ncomms12406.

55. Clinical and Laboratory Standards Institute (CLSI.) 2015. M07-A10: methods for dilution antimicrobial susceptibility tests for bacteria that grow aerobically; approved standard-10th ed CLSI, Wayne, Pa.

56. Clinical and Laboratory Standards Institute (CLSI.) 2015. M100-S25: performance standards for antimicrobial susceptibility testing; 25th informational supplement. CLSI, Wayne, Pa.

57. van Berke/ S.S. et al., Assay Platform for Clinically Relevant Metallo-β-lactamases, J. Med. Chem., 2013, 56 (17), pp 6945-6953.

The invention claimed is:

1. A combination therapeutic product comprising a β-lactamase inhibitor of Formula Ic, or a pharmaceutically acceptable salt thereof, and one or more β-lactam antibiotics, wherein the β-lactamase inhibitor of Formula Ic has the structural formula shown below:

Formula Ic wherein:
n is 0 or 1;
$R_1$ is a substituent group of the formula:

—X—Z wherein
X is —N($R^{43}$)—C(O), wherein $R^{43}$ is selected from hydrogen or (1-2C)alkyl; and
Z is (1-6C)alkyl, aryl or (3-6C)cycloalkyl;
and wherein Z is optionally further substituted by one or more substituent groups independently selected from oxo, halo, cyano, nitro, hydroxy, carboxy, $NR^{46}R^{47}$, —$(CH_2)_p$—$NR^{46}R^{47}$ (wherein p is selected from 1 or 2 (1-4C)alkoxy, (1-4C)alkyl or (1-4C)alkanoyl; wherein $R^{46}$ and $R^{47}$ are each independently selected from hydrogen, (1-4C)alkyl or (1-4C)alkylamino; and
$R_2$ is a substituent of the formula —C(O)O$R_{2A}$, wherein $R_{2A}$ is selected from hydrogen, (1-6C)alkyl or (3-8C)cycloalkyl.

2. A combination therapeutic product according to claim 1, wherein the β-lactamase inhibitor is selected from one of the following compounds, or a pharmaceutically acceptable salt thereof:

3. A combination therapeutic product according to claim 1, wherein the β-lactam antibiotic is selected from one or more of azetreonam, temocillin, piperacillin, cefpodoxime, ceftazidime, cefotaxime, ceftriaxone, meropenem, faropenem, imipenem, loracarbef, ceftobiprole or ceftaroline.

4. A combination therapeutic product according to claim 3, wherein the one or more β-lactam antibiotic is selected from azetreonam, ceftazidime or meropenem.

5. A pharmaceutical composition comprising a combination therapeutic product according to claim 1, or a compound of Formula Ic according to claim 1, in association with a pharmaceutically-acceptable excipient or carrier.

6. A combination therapeutic product according to claim 1, wherein $R_2$ is COOH.

7. A combination therapeutic product according to claim 1, wherein n is 1.

* * * * *